United States Patent
Haines

(10) Patent No.: US 9,814,539 B2
(45) Date of Patent: Nov. 14, 2017

(54) METHODS AND APPARATUS FOR CONFORMABLE PROSTHETIC IMPLANTS

(75) Inventor: Timothy G. Haines, Seattle, WA (US)

(73) Assignee: Puget BioVentures LLC, Saratoga Springs, NY (US)

( * ) Notice: Subject to any disclaimer, the term of this patent is extended or adjusted under 35 U.S.C. 154(b) by 836 days.

(21) Appl. No.: 11/075,840

(22) Filed: Mar. 8, 2005

(65) Prior Publication Data

US 2006/0058882 A1    Mar. 16, 2006
US 2016/0302933 A9    Oct. 20, 2016

Related U.S. Application Data

(63) Continuation-in-part of application No. 11/036,584, filed on Jan. 14, 2005, now Pat. No. 7,815,645, (Continued)

(51) Int. Cl.
    *A61F 2/30*      (2006.01)
    *A61B 17/58*      (2006.01)
    (Continued)

(52) U.S. Cl.
    CPC .......... *A61B 90/10* (2016.02); *A61B 17/1757* (2013.01); *A61B 17/1764* (2013.01);
    (Continued)

(58) Field of Classification Search
    CPC .......... A61F 2/3859; A61F 2/389; A61F 2/38; A61F 2/30942; A61F 2310/00011; A61F 2/3886; A61F 2002/30934; A61F 2/30
    (Continued)

(56) References Cited

U.S. PATENT DOCUMENTS 2,697,433 A    12/1954    Zehnder
3,457,922 A    7/1969    Ray
(Continued)

FOREIGN PATENT DOCUMENTS

EP    0104732    4/1984
EP    0121142    10/1984
(Continued)

OTHER PUBLICATIONS

*Hudson Surgical Design v. Zimmer Holdings, Inc.*, et al., Zimmer, Inc.'s and Zimmer Holding Inc's Supplemental Responses to Hudson Surgical Design, Inc.'s First Set of Interrogatories (Nos. 1-18) to Each of Them, dated Aug. 1, 2008.
(Continued)

*Primary Examiner* — Ann Schillinger
(74) *Attorney, Agent, or Firm* — Patterson Thuente Pedersen, P.A.

(57) ABSTRACT

A biomechanical optimization (BMO) prosthetic implant utilizes a thin cross-section of metallic material that is conformable. Preferably, the BMO prosthetic implant is conformable both at the time of implant in response to manipulation and fixation by the surgeon, as well as during the life of the implant in response to stresses and loads experienced by the implant and thereby communicated and responded to by living bone tissue. For most metallic alloys, the BMO prosthetic implant will have an effective cross-sectional thickness of 4 mm or less, and preferably 3 mm or less. In one embodiment, the BMO prosthetic implant is provided with one or more fins extending from the fixation surface(s) of the implant which preferably includes retaining structures, such as cross-pinned apertures or T-shaped edge ridge.

28 Claims, 18 Drawing Sheets

Related U.S. Application Data application No. 11/075,840, which is a continuation-in-part of application No. 11/049,634, filed on Feb. 2, 2005, now abandoned.

(60) Provisional application No. 60/551,631, filed on Mar. 8, 2004, provisional application No. 60/551,080, filed on Mar. 8, 2004, provisional application No. 60/551,078, filed on Mar. 8, 2004, provisional application No. 60/551,096, filed on Mar. 8, 2004, provisional application No. 60/551,307, filed on Mar. 8, 2004, provisional application No. 60/551,262, filed on Mar. 8, 2004, provisional application No. 60/551,160, filed on Mar. 8, 2004, provisional application No. 60/536,320, filed on Jan. 14, 2005, provisional application No. 60/540,992, filed on Feb. 2, 2004.

(51) Int. Cl.
*A61B 90/10* (2016.01)
*A61B 17/17* (2006.01)
*A61F 2/38* (2006.01)
*A61B 17/16* (2006.01)

(52) U.S. Cl.
CPC .............. *A61F 2/38* (2013.01); *A61F 2/3859* (2013.01); *A61B 17/1671* (2013.01); *A61B 17/1675* (2013.01); *A61B 2017/1602* (2013.01); *A61F 2002/30649* (2013.01); *A61F 2002/3895* (2013.01); *A61F 2310/00011* (2013.01)

(58) Field of Classification Search
USPC ................................. 623/20.14–20.34, 13.12
See application file for complete search history.

(56) References Cited

U.S. PATENT DOCUMENTS

| | | | |
|---|---|---|---|
| 3,739,662 A | 6/1973 | Windelman et al. | |
| 3,748,662 A | 7/1973 | Helfet | |
| 3,774,244 A | 11/1973 | Walker | |
| 3,798,679 A | 3/1974 | Ewald | |
| 3,816,855 A | 6/1974 | Salch | |
| 3,906,550 A * | 9/1975 | Rostoker et al. | 623/23.55 |
| 3,943,934 A | 3/1976 | Bent | |
| 3,953,899 A * | 5/1976 | Charnley | 623/20.3 |
| 3,958,278 A | 5/1976 | Lee | |
| 3,977,289 A | 8/1976 | Tuke | |
| 4,000,525 A * | 1/1977 | Klawitter et al. | 623/20.32 |
| 4,016,606 A | 4/1977 | Murray | |
| 4,069,824 A | 1/1978 | Weinstock | |
| 4,178,641 A | 12/1979 | Gruendel | |
| 4,207,627 A | 6/1980 | Cloutier | |
| 4,213,209 A | 7/1980 | Insall | |
| 4,249,270 A | 2/1981 | Bahler | |
| 4,340,978 A * | 7/1982 | Buechel et al. | 623/20.29 |
| 4,349,058 A | 9/1982 | Comparetto | |
| 4,353,135 A | 10/1982 | Forte | |
| 4,358,859 A | 11/1982 | Schurman et al. | |
| 4,421,112 A | 12/1983 | Mains | |
| 4,457,307 A | 7/1984 | Stillwell | |
| 4,474,177 A | 10/1984 | Whiteside | |
| 4,479,271 A * | 10/1984 | Bolesky et al. | 623/20.17 |
| 4,487,203 A | 12/1984 | Androphy | |
| 4,501,266 A | 2/1985 | McDaniel | |
| 4,502,483 A | 3/1985 | Lacey | |
| 4,524,766 A | 6/1985 | Petersen | |
| 4,566,448 A | 1/1986 | Rohr, Jr. | |
| 4,567,886 A | 2/1986 | Peterson | |
| 4,568,348 A | 2/1986 | Johnson et al. | |
| 4,584,999 A | 4/1986 | Arneggar | |
| 4,586,496 A | 5/1986 | Keller | |
| 4,586,933 A | 5/1986 | Shoji et al. | |
| 4,653,488 A | 3/1987 | Kenna | |
| 4,659,331 A * | 4/1987 | Matthews et al. | 623/20.21 |
| 4,662,889 A | 5/1987 | Zichner | |
| 4,693,721 A * | 9/1987 | Ducheyne | 623/23.54 |
| 4,703,751 A | 11/1987 | Pohl | |
| 4,709,699 A | 12/1987 | Michael et al. | |
| 4,711,639 A | 12/1987 | Grundei | |
| 4,714,472 A | 12/1987 | Averill | |
| 4,714,473 A | 12/1987 | Bloebaum | |
| 4,718,413 A | 1/1988 | Johnson | |
| 4,721,104 A | 1/1988 | Kaufman | |
| 4,722,330 A | 2/1988 | Russell | |
| 4,731,086 A * | 3/1988 | Whiteside et al. | 623/20.16 |
| 4,736,086 A | 4/1988 | Obara | |
| 4,736,737 A | 4/1988 | Fargie | |
| 4,738,256 A | 4/1988 | Freeman | |
| 4,759,350 A | 7/1988 | Dunn | |
| 4,770,663 A | 9/1988 | Hanslik | |
| 4,787,383 A | 11/1988 | Kenna | |
| 4,808,185 A | 2/1989 | Penenberg | |
| 4,822,365 A | 4/1989 | Walker | |
| 4,834,758 A | 5/1989 | Lane | |
| 4,841,975 A | 6/1989 | Woolson | |
| 4,880,429 A * | 11/1989 | Stone | 623/14.12 |
| 4,892,093 A | 1/1990 | Zarnowski | |
| 4,893,619 A | 1/1990 | Dale | |
| 4,896,663 A | 1/1990 | Vandewalle | |
| 4,919,667 A * | 4/1990 | Richmond | 623/14.12 |
| 4,926,847 A | 5/1990 | Luckman | |
| 4,935,023 A | 6/1990 | Whiteside | |
| 4,936,853 A | 6/1990 | Fabian | |
| 4,938,762 A | 7/1990 | Wehrli | |
| 4,938,769 A | 7/1990 | Shaw | |
| 4,944,757 A | 7/1990 | Martinez | |
| 4,950,298 A | 8/1990 | Gustilo | |
| 4,952,213 A | 8/1990 | Bowman | |
| 4,963,152 A | 10/1990 | Hofmann | |
| 4,963,153 A | 10/1990 | Noesberger | |
| 4,971,075 A | 11/1990 | Lee | |
| 4,979,949 A | 12/1990 | Matsen | |
| 4,986,833 A | 1/1991 | Worland | |
| 5,002,545 A | 3/1991 | Whiteside | |
| 5,002,547 A | 3/1991 | Poggie | |
| 5,007,933 A | 4/1991 | Sidebotham | |
| 5,007,934 A * | 4/1991 | Stone | 623/14.12 |
| 5,021,056 A | 6/1991 | Hofman | |
| 5,021,061 A | 6/1991 | Wevers | |
| 5,032,134 A * | 7/1991 | Lindwer | 623/23.36 |
| 5,041,138 A * | 8/1991 | Vacanti et al. | 424/422 |
| 5,047,032 A | 9/1991 | Jellicoe | |
| 5,049,149 A | 9/1991 | Schmidt | |
| 5,053,037 A | 10/1991 | Lackey | |
| 5,059,037 A | 10/1991 | Albert | |
| 5,062,852 A | 11/1991 | Dorr | |
| 5,080,675 A | 1/1992 | Lawes | |
| 5,092,869 A | 3/1992 | Waldron | |
| 5,098,436 A | 3/1992 | Ferrante | |
| 5,100,409 A | 3/1992 | Coates | |
| 5,108,398 A | 4/1992 | McQueen | |
| 5,112,336 A | 5/1992 | Krevolin | |
| 5,116,375 A | 5/1992 | Hofmann | |
| 5,122,144 A | 6/1992 | Bert | |
| 5,129,909 A | 7/1992 | Sutherland | |
| 5,133,758 A | 7/1992 | Hollister | |
| 5,133,759 A | 7/1992 | Turner | |
| 5,137,536 A | 8/1992 | Koshino | |
| 5,147,364 A | 9/1992 | Comparetto | |
| 5,147,365 A | 9/1992 | Whitlock | |
| 5,147,405 A | 9/1992 | Van Zile | |
| 5,176,710 A * | 1/1993 | Hahn et al. | 623/20.32 |
| 5,178,626 A | 1/1993 | Pappas | |
| 5,190,547 A | 3/1993 | Barber, Jr. | |
| 5,197,944 A | 3/1993 | Steele | |
| 5,201,881 A | 4/1993 | Evans | |
| 5,203,807 A | 4/1993 | Evans | |
| 5,206,023 A * | 4/1993 | Hunziker | 424/423 |
| 5,219,362 A | 6/1993 | Tuke | |
| 5,226,916 A | 7/1993 | Goodfellow | |

(56) References Cited

U.S. PATENT DOCUMENTS

| | | | |
|---|---|---|---|
| 5,228,459 A | 7/1993 | Caspari | |
| 5,234,432 A | 8/1993 | Brown | |
| 5,234,433 A | 8/1993 | Bert | |
| 5,236,432 A | 8/1993 | Matsen | |
| 5,236,461 A | 8/1993 | Forte | |
| 5,236,875 A | 8/1993 | Trigg | |
| 5,250,050 A | 10/1993 | Poggie | |
| 5,263,498 A | 11/1993 | Caspari | |
| 5,263,956 A | 11/1993 | Nobles | |
| 5,269,786 A | 12/1993 | Morgan | |
| 5,275,603 A | 1/1994 | Ferrante | |
| 5,279,575 A | 1/1994 | Sugarbaker | |
| 5,282,803 A | 2/1994 | Lackey | |
| 5,282,867 A | 2/1994 | Mikhail | |
| 5,284,482 A | 2/1994 | Mikhail | |
| 5,304,181 A | 4/1994 | Caspari | |
| 5,306,276 A | 4/1994 | Johnson | |
| 5,314,482 A | 5/1994 | Goodfellow | |
| 5,326,358 A | 7/1994 | Aubriot | |
| 5,330,533 A | 7/1994 | Walker | |
| 5,330,534 A | 7/1994 | Herrington | |
| 5,342,368 A | 8/1994 | Peterson | |
| 5,358,527 A | 10/1994 | Forte | |
| 5,358,529 A * | 10/1994 | Davidson | 623/20.19 |
| 5,358,531 A | 10/1994 | Goodfellow | |
| 5,364,401 A | 11/1994 | Ferreante | |
| 5,364,402 A | 11/1994 | Mumme | |
| 5,370,699 A | 12/1994 | Hood | |
| 5,370,701 A | 12/1994 | Fin | |
| 5,391,170 A | 2/1995 | McGuire | |
| 5,397,330 A | 3/1995 | Mikhail | |
| 5,405,349 A | 4/1995 | Burkinshaw | |
| 5,413,604 A | 5/1995 | Hodge | |
| 5,415,663 A | 5/1995 | Luckman | |
| 5,417,694 A | 5/1995 | Marik | |
| 5,417,695 A | 5/1995 | Axelson, Jr. | |
| 5,443,464 A | 8/1995 | Russell | |
| 5,454,816 A | 10/1995 | Ashby | |
| 5,462,551 A | 10/1995 | Bailey | |
| 5,470,335 A | 11/1995 | Du Toit | |
| 5,474,559 A | 12/1995 | Bertin | |
| 5,480,446 A | 1/1996 | Goodfellow | |
| 5,514,136 A | 5/1996 | Richelsoph | |
| 5,514,139 A | 5/1996 | Goldstein et al. | |
| 5,514,143 A | 5/1996 | Bonutti | |
| 5,520,694 A | 5/1996 | Dance | |
| 5,520,695 A | 5/1996 | Luckman | |
| 5,540,695 A | 7/1996 | Levy | |
| 5,542,947 A | 8/1996 | Treacy | |
| 5,549,683 A | 8/1996 | Bonutti | |
| 5,549,684 A | 8/1996 | Amino | |
| 5,549,688 A | 8/1996 | Ries | |
| 5,551,429 A | 9/1996 | Fitzpatrick | |
| 5,562,674 A | 10/1996 | Stalcup | |
| 5,569,262 A | 10/1996 | Carney | |
| 5,571,100 A | 11/1996 | Goble et al. | |
| 5,578,039 A | 11/1996 | Vendrely | |
| 5,593,411 A | 1/1997 | Stalcup | |
| 5,597,379 A | 1/1997 | Haines | |
| 5,597,397 A | 1/1997 | Funk et al. | |
| 5,601,563 A | 2/1997 | Burke | |
| 5,601,566 A | 2/1997 | Dance | |
| 5,609,645 A | 3/1997 | Vinciguerra | |
| 5,611,802 A | 3/1997 | Samuelson | |
| 5,613,969 A | 3/1997 | Jenkins, Jr. | |
| 5,628,749 A | 5/1997 | Vendrely | |
| 5,639,279 A | 6/1997 | Burkinshaw | |
| 5,643,272 A | 7/1997 | Haines | |
| 5,649,928 A | 7/1997 | Grundei | |
| 5,653,714 A | 8/1997 | Dietz et al. | |
| 5,658,293 A | 8/1997 | Vanlaningham | |
| 5,667,511 A | 9/1997 | Vendrely | |
| 5,681,354 A | 10/1997 | Eckhoff | |
| 5,682,886 A | 11/1997 | Delp | |
| 5,690,632 A | 11/1997 | Schwartz | |
| 5,690,635 A | 11/1997 | Matsen, III | |
| 5,690,637 A | 11/1997 | Wen | |
| 5,697,935 A | 12/1997 | Moran | |
| 5,702,458 A | 12/1997 | Burstein | |
| 5,723,016 A | 3/1998 | Minns | |
| 5,725,530 A | 3/1998 | Popken | |
| 5,728,162 A | 3/1998 | Eckhoff | |
| 5,755,801 A | 5/1998 | Walker | |
| 5,755,803 A * | 5/1998 | Haines et al. | 623/20.14 |
| 5,755,804 A | 5/1998 | Schmotzer | |
| 5,766,257 A | 6/1998 | Goodman | |
| 5,768,134 A | 6/1998 | Swaelens et al. | |
| 5,769,855 A | 6/1998 | Bertin et al. | |
| 5,769,899 A * | 6/1998 | Schwartz et al. | 606/77 |
| 5,776,200 A | 7/1998 | Johnson | |
| 5,782,921 A | 7/1998 | Colleran | |
| 5,782,925 A | 7/1998 | Collaz | |
| 5,799,055 A | 8/1998 | Peshkin et al. | |
| 5,800,552 A | 9/1998 | Forte | |
| 5,810,827 A | 9/1998 | Haines et al. | |
| 5,824,100 A | 10/1998 | Kester | |
| 5,824,102 A | 10/1998 | Buscayret | |
| 5,824,105 A | 10/1998 | Ries | |
| 5,871,545 A | 2/1999 | Goodfellow | |
| 5,871,546 A | 2/1999 | Colleran | |
| 5,879,354 A | 3/1999 | Haines | |
| 5,879,392 A | 3/1999 | McMinn | |
| 5,906,643 A | 5/1999 | Walker | |
| 5,908,424 A | 6/1999 | Bertin | |
| 5,925,049 A | 7/1999 | Gustilo | |
| 5,935,173 A | 8/1999 | Roger | |
| 5,944,758 A | 8/1999 | Mansat | |
| 5,954,770 A | 9/1999 | Schmotzer | |
| 5,980,526 A | 11/1999 | Johnson | |
| 5,986,169 A | 11/1999 | Gjunter | |
| 5,997,577 A | 12/1999 | Herrington | |
| 6,039,764 A | 3/2000 | Pottenger | |
| 6,056,754 A | 5/2000 | Haines | |
| 6,059,788 A | 5/2000 | Katz | |
| 6,068,658 A | 5/2000 | Insall | |
| 6,080,195 A | 6/2000 | Colleran | |
| 6,083,228 A | 7/2000 | Michelson | |
| 6,099,570 A | 8/2000 | Livet | |
| 6,110,182 A | 8/2000 | Mowlai-Ashtiani | |
| 6,120,543 A | 9/2000 | Meesenburg | |
| 6,132,468 A * | 10/2000 | Mansmann | 623/20.16 |
| 6,139,581 A | 10/2000 | Engh | |
| 6,165,223 A | 12/2000 | Metzger | |
| 6,171,340 B1 * | 1/2001 | McDowell | 623/18.11 |
| 6,195,577 B1 | 2/2001 | Truwit | |
| 6,197,064 B1 | 3/2001 | Haines | |
| 6,203,576 B1 | 3/2001 | Afriat | |
| 6,206,926 B1 | 3/2001 | Pappas | |
| 6,210,443 B1 | 4/2001 | Marceaux | |
| 6,235,060 B1 | 5/2001 | Meesenburg | |
| 6,236,875 B1 | 5/2001 | Becholz | |
| 6,264,697 B1 | 7/2001 | Walker | |
| 6,285,902 B1 | 9/2001 | Kienzle, III et al. | |
| 6,306,146 B1 | 10/2001 | Dinkler | |
| 6,306,172 B1 | 10/2001 | O'Neil | |
| 6,325,828 B1 | 12/2001 | Dennis | |
| 6,340,363 B1 | 1/2002 | Bolger et al. | |
| 6,342,075 B1 * | 1/2002 | MacArthur | 623/20.14 |
| 6,348,058 B1 | 2/2002 | Melkent et al. | |
| 6,361,564 B1 | 3/2002 | Marceaux | |
| 6,368,353 B1 | 4/2002 | Arcand | |
| 6,375,658 B1 * | 4/2002 | Hangody et al. | 606/80 |
| 6,379,388 B1 | 4/2002 | Ensign | |
| 6,401,346 B1 | 6/2002 | Roberts | |
| 6,406,497 B2 | 6/2002 | Takei | |
| 6,413,279 B1 | 7/2002 | Metzger | |
| 6,430,434 B1 | 8/2002 | Mittelstadt | |
| 6,436,145 B1 | 8/2002 | Miller | |
| 6,443,991 B1 | 9/2002 | Running | |
| 6,458,128 B1 | 10/2002 | Schulze | |
| 6,470,207 B1 | 10/2002 | Simon et al. | |
| 6,475,241 B2 | 11/2002 | Pappas | |
| 6,477,400 B1 | 11/2002 | Barrick | |
| 6,482,209 B1 | 11/2002 | Engh | |

(56) References Cited

U.S. PATENT DOCUMENTS

| | | | |
|---|---|---|---|
| 6,482,409 B1 | 11/2002 | Lobb et al. | |
| 6,485,519 B2 | 11/2002 | Meyers | |
| 6,491,699 B1 | 12/2002 | Henderson et al. | |
| 6,491,726 B2 | 12/2002 | Pappas | |
| 6,500,208 B1 | 12/2002 | Metzger | |
| 6,506,215 B1 | 1/2003 | Letot | |
| 6,520,964 B2* | 2/2003 | Tallarida et al. | 606/71 |
| 6,554,838 B2 | 4/2003 | McGovern | |
| 6,575,980 B1 | 6/2003 | Robie | |
| 6,579,290 B1* | 6/2003 | Hardcastle et al. | 606/247 |
| 6,595,997 B2 | 7/2003 | Axelson et al. | |
| 6,620,198 B2 | 9/2003 | Burstein | |
| 6,623,526 B1 | 9/2003 | Lloyd | |
| 6,645,251 B2 | 11/2003 | Salehi | |
| 6,679,917 B2* | 1/2004 | Ek | 623/20.14 |
| 6,685,711 B2 | 2/2004 | Axelson, Jr. et al. | |
| 6,694,168 B2 | 2/2004 | Traxel | |
| 6,694,768 B2 | 2/2004 | Lu | |
| 6,695,848 B2 | 2/2004 | Haines | |
| 6,697,664 B2 | 2/2004 | Kienzle, III | |
| 6,701,174 B1 | 3/2004 | Krause et al. | |
| 6,702,821 B2 | 3/2004 | Bonutti | |
| 6,711,432 B1 | 3/2004 | Krause et al. | |
| 6,725,080 B2 | 4/2004 | Melkent et al. | |
| 6,755,563 B2 | 6/2004 | Wahlig | |
| 6,755,835 B2 | 6/2004 | Schultheiss | |
| 6,755,864 B1 | 6/2004 | Brack | |
| 6,672,224 B2 | 7/2004 | Tallarida | |
| 6,764,516 B2 | 7/2004 | Pappas | |
| 6,770,097 B2 | 8/2004 | Leclercq | |
| 6,773,461 B2 | 8/2004 | Meyers | |
| 6,783,550 B2* | 8/2004 | MacArthur | 623/20.14 |
| 6,796,988 B2 | 9/2004 | Melkent et al. | |
| 6,827,723 B2 | 12/2004 | Carson | |
| 6,858,032 B2 | 2/2005 | Chow | |
| 6,875,222 B2 | 4/2005 | Long | |
| 6,886,684 B2 | 5/2005 | Hacikyan | |
| 6,898,858 B1 | 5/2005 | Spell | |
| 6,911,044 B2 | 6/2005 | Fell | |
| 6,916,324 B2 | 7/2005 | Sanford | |
| 6,916,340 B2 | 7/2005 | Metzger | |
| 6,942,627 B2 | 9/2005 | Huitema | |
| 6,942,694 B2 | 9/2005 | Liddicoat | |
| 7,018,418 B2 | 3/2006 | Amrich | |
| 7,029,477 B2 | 4/2006 | Grimm | |
| 7,048,741 B2 | 5/2006 | Swanson | |
| 7,060,074 B2 | 6/2006 | Rosa | |
| 7,077,867 B1* | 7/2006 | Pope et al. | 623/20.14 |
| 7,104,966 B2 | 9/2006 | Shilber | |
| 7,141,053 B2 | 11/2006 | Rosa | |
| 7,172,596 B2 | 2/2007 | Coon | |
| 7,175,630 B2 | 2/2007 | Farling | |
| 7,241,298 B2 | 7/2007 | Nemec | |
| 7,247,157 B2 | 7/2007 | Prager | |
| 7,326,252 B2 | 2/2008 | Otto | |
| 7,344,541 B2 | 3/2008 | Haines | |
| 7,371,240 B2 | 5/2008 | Pinczewski | |
| 7,422,605 B2 | 9/2008 | Burstein | |
| 7,491,235 B2 | 2/2009 | Fell | |
| 7,618,451 B2 | 11/2009 | Berez et al. | |
| 7,922,771 B2 | 4/2011 | Otto | |
| 8,021,368 B2 | 9/2011 | Haines | |
| 2001/0018615 A1 | 8/2001 | Biegun | |
| 2001/0044627 A1 | 11/2001 | Justin | |
| 2001/0049558 A1 | 12/2001 | Liddicoat | |
| 2002/0029038 A1 | 3/2002 | Haines | |
| 2002/0055783 A1* | 5/2002 | Tallarida et al. | 623/20.14 |
| 2002/0055784 A1 | 5/2002 | Burstein | |
| 2002/0103541 A1 | 8/2002 | Meyers | |
| 2002/0107576 A1 | 8/2002 | Meyers | |
| 2002/0120340 A1 | 8/2002 | Metzger | |
| 2002/0161447 A1 | 10/2002 | Salehi | |
| 2002/0183760 A1 | 12/2002 | McGovern | |
| 2003/0028196 A1 | 2/2003 | Bonutti | |
| 2003/0045883 A1 | 3/2003 | Chow et al. | |
| 2003/0055501 A1 | 3/2003 | Fell | |
| 2003/0055509 A1 | 3/2003 | McCue | |
| 2003/0060882 A1 | 3/2003 | Fell | |
| 2003/0060883 A1 | 3/2003 | Fell | |
| 2003/0060884 A1 | 3/2003 | Fell | |
| 2003/0060885 A1 | 3/2003 | Fell | |
| 2003/0065401 A1* | 4/2003 | Amrich et al. | 623/23.55 |
| 2003/0069585 A1 | 4/2003 | Axelson et al. | |
| 2003/0069591 A1 | 4/2003 | Carson et al. | |
| 2003/0075564 A1 | 4/2003 | Wahlig et al. | |
| 2003/0093156 A1 | 5/2003 | Metzger | |
| 2003/0100906 A1 | 5/2003 | Rosa et al. | |
| 2003/0130665 A1 | 7/2003 | Pinczewski | |
| 2003/0158606 A1 | 8/2003 | Coon | |
| 2003/0171757 A1 | 9/2003 | Coon et al. | |
| 2003/0181986 A1 | 9/2003 | Buchholz | |
| 2003/0208122 A1 | 11/2003 | Melkent | |
| 2003/0212403 A1 | 11/2003 | Swanson | |
| 2003/0212413 A1 | 11/2003 | Wilk | |
| 2004/0039396 A1 | 2/2004 | Couture et al. | |
| 2004/0044414 A1 | 3/2004 | Nowakowski | |
| 2004/0122305 A1 | 6/2004 | Grimm et al. | |
| 2004/0122436 A1 | 6/2004 | Grimm | |
| 2004/0152970 A1 | 8/2004 | Hunter et al. | |
| 2004/0153066 A1 | 8/2004 | Coon et al. | |
| 2004/0153083 A1 | 8/2004 | Nemer et al. | |
| 2004/0153085 A1 | 8/2004 | Farling et al. | |
| 2004/0199249 A1 | 10/2004 | Fell | |
| 2004/0199250 A1* | 10/2004 | Fell | 623/14.12 |
| 2004/0249467 A1 | 12/2004 | Meyers | |
| 2004/0249471 A1* | 12/2004 | Bindseil et al. | 623/23.51 |
| 2004/0267363 A1 | 12/2004 | Fell | |
| 2005/0027365 A1* | 2/2005 | Burstein et al. | 623/20.32 |
| 2005/0033424 A1 | 2/2005 | Fell | |
| 2005/0149038 A1 | 7/2005 | Haines | |
| 2005/0149039 A1 | 7/2005 | Haines | |
| 2005/0149040 A1 | 7/2005 | Haines | |
| 2005/0171604 A1* | 8/2005 | Michalow | 623/14.12 |
| 2005/0283251 A1 | 12/2005 | Coon | |
| 2006/0015109 A1 | 1/2006 | Haines | |
| 2006/0015115 A1 | 1/2006 | Haines | |
| 2006/0015116 A1 | 1/2006 | Haines | |
| 2006/0015117 A1 | 1/2006 | Haines | |
| 2006/0030853 A1 | 2/2006 | Haines | |
| 2006/0030854 A1 | 2/2006 | Haines | |
| 2006/0030855 A1 | 2/2006 | Haines | |
| 2006/0030944 A1 | 2/2006 | Haines | |
| 2006/0052875 A1* | 3/2006 | Bernero et al. | 623/20.33 |
| 2006/0058882 A1 | 3/2006 | Haines | |
| 2007/0078517 A1 | 4/2007 | Engh et al. | |
| 2007/0179607 A1 | 8/2007 | Hodorek et al. | |
| 2008/0154270 A1 | 6/2008 | Haines | |
| 2009/0076514 A1 | 3/2009 | Haines | |
| 2009/0082773 A1 | 3/2009 | Haines | |
| 2009/0138018 A1 | 5/2009 | Haines | |
| 2010/0100192 A1 | 4/2010 | Haines | |

FOREIGN PATENT DOCUMENTS

| | | |
|---|---|---|
| EP | 0189253 | 7/1986 |
| EP | 0243109 | 10/1987 |
| EP | 0327249 | 8/1989 |
| EP | 0337901 | 10/1989 |
| EP | 0380451 | 1/1990 |
| EP | 0941719 | 9/1990 |
| EP | 0415837 | 3/1991 |
| EP | 0466659 A2 | 1/1992 |
| EP | 0538153 A1 | 4/1993 |
| EP | 0555003 | 8/1993 |
| EP | 556998 | 8/1993 |
| EP | 0682916 A2 | 11/1995 |
| EP | 0761242 A1 | 3/1997 |
| EP | 0916321 | 5/1999 |
| EP | 0923916 | 6/1999 |
| EP | 0970667 | 1/2000 |
| EP | 0988840 | 3/2000 |
| FR | 2635675 | 3/1990 |
| FR | 2664157 A1 | 1/1992 |
| FR | 2701387 | 8/1994 |

(56) References Cited

FOREIGN PATENT DOCUMENTS

| | | |
|---|---|---|
| FR | 2710258 | 3/1995 |
| FR | 2760352 | 9/1998 |
| GB | 1409150 | 10/1975 |
| GB | 2007980 B | 7/1982 |
| GB | 2296443 | 7/1996 |
| GB | 2324249 | 10/1998 |
| GB | 2335145 | 9/1999 |
| JP | 02-501806 | 1/1983 |
| JP | 58-209343 | 12/1983 |
| JP | 61-170453 | 8/1986 |
| JP | 62-133948 | 6/1987 |
| JP | 62-254750 | 6/1987 |
| JP | 01-119244 | 5/1989 |
| JP | 01-126957 | 5/1989 |
| JP | 01-209055 | 8/1989 |
| JP | 02-057247 | 2/1990 |
| JP | 02-234756 | 9/1990 |
| JP | 02-234757 | 9/1990 |
| JP | 02-243143 | 9/1990 |
| JP | 239861 | 9/1990 |
| JP | 02-246971 | 10/1990 |
| JP | 2002/274214 A | 11/1990 |
| JP | 03-032663 | 2/1991 |
| JP | 04-297254 | 10/1992 |
| JP | 04-361746 | 12/1992 |
| JP | 05-003880 | 1/1993 |
| JP | 05-502814 | 5/1993 |
| JP | 5-41510 | 6/1993 |
| JP | 05-269140 | 10/1993 |
| JP | 05-277130 | 10/1993 |
| JP | 06-08033 | 1/1994 |
| JP | 06-38971 | 2/1994 |
| JP | 6-217984 | 8/1994 |
| JP | 06-233775 | 8/1994 |
| JP | 06-237941 | 8/1994 |
| JP | 7-501966 | 3/1995 |
| JP | 7-116185 | 5/1995 |
| JP | 7-136200 | 5/1995 |
| RU | 2121319 | 11/1998 |
| SE | 382155 | 1/1976 |
| SU | 577020 T | 10/1977 |
| WO | WO 81/03122 | 11/1981 |
| WO | WO 91/00061 | 1/1991 |
| WO | WO 91/10408 | 7/1991 |
| WO | WO 93/22990 | 11/1993 |
| WO | WO 93/25157 | 12/1993 |
| WO | WO 93/25157 A1 | 12/1993 |
| WO | WO 94/05212 | 3/1994 |
| WO | WO 94/08528 | 4/1994 |
| WO | WO 94/09730 | 5/1994 |
| WO | WO 94/14366 | 7/1994 |
| WO | WO 94/22397 | 10/1994 |
| WO | WO96/01588 | 1/1996 |
| WO | WO96/07361 A1 | 3/1996 |
| WO | WO 96/24295 | 8/1996 |
| WO | WO97/05827 | 2/1997 |
| WO | WO97/29703 A1 | 8/1997 |
| WO | WO97/29704 A1 | 8/1997 |
| WO | WO 9820817 | 5/1998 |
| WO | WO 99/27872 | 6/1999 |
| WO | WO 99/30649 | 6/1999 |
| WO | WO 01/13825 | 3/2001 |
| WO | WO02/34310 A2 | 5/2002 |
| WO | WO2004/069036 | 8/2004 |
| WO | WO2004/070580 | 8/2004 |
| WO | WO2004/100758 | 11/2004 |
| WO | WO2004/100839 | 11/2004 |

OTHER PUBLICATIONS

Hudson Surgical Design v. Zimmer Holdings, Inc., et al., Revised Final Claim Construction Chart, dated Mar. 11, 2009.

T.D.V. Cooke et al., Universal Bone Cutting Device for Precision Knee Replacement Arthroplasty and Osteotomy, 7 J. Biomed. Eng'g 45, 47, col. 2, ll. 52-57 (1985).
E. Marlowe Goble and Daniel F. Justin, Minimally invasive total knee replacement: principles and technique, Orthop. Clin. N. Am. 35 (2004) 235-245.
Whiteside Ortholoc Total Knee System: Surgical Procedure, Dow Corning Wright, pp. WMT000001-WMT000040, Jun. 1985.
Zimmer, Insall/Burstein II, Constrained Condylar: Modular Knee System, 35 pages, copyright 1989.
Application and File History of U.S. Appl. No. 12/187,210, filed Aug. 6, 2008.
Application and File History of U.S. Appl. No. 11/075,842, filed Mar. 8, 2005.
Application and File History of U.S. Appl. No. 11/075,828, filed Mar. 8, 2005.
Application and File History of U.S. Appl. No. 11/075,836, filed Mar. 8, 2005.
Application and File History of U.S. Appl. No. 11/075,552, Inventor: Haines, filed Mar. 8, 2005.
Application and File History of U.S. Appl. No. 11/036,584, filed Jan. 14, 2005.
Application and File History of U.S. Appl. No. 11/049,634, filed Feb. 5, 2005.
Application and File History of U.S. Appl. No. 11/074,599, filed Mar. 8, 2005.
Application and File History of U.S. Appl. No. 11/075,553, filed Mar. 8, 2005.
Application and File History of U.S. Appl. No. 11/825,857, Inventor: Haines, filed Jul. 9, 2007.
Application and File History of U.S. Appl. No. 12/171,843, Inventor: Haines, filed Jul. 11, 2008.
Whiteside Ortholoc Total Knee System, Dow Corning Wright, pp. ZH000109679-ZH000109690.
Zimmer, Insall/Burstein II, Modular Knee System, Surgical Technique, pp. ZH000109691-ZH000109710.
Zimmer, The Miller/Galante Advantage: Total Knee System, pp. ZH000159653-ZH000159668.
Application and File History of U.S. Appl. No. 12/757,778, Inventor: Haines, filed Apr. 9, 2010.
Application and File History of U.S. Appl. No. 12/638,692, Inventor: Haines, filed Dec. 15, 2009.
Zimmer, The Best Thing Next to Bone, Updated Mar. 3, 2009, 5 pages, © 2010, www.zimmer.com.
Freeman Samuelson, Total Knee System, published by Biomet, Inc., 1994 ("Biomet Brochure") (Attached as Exhibit F).
Freeman, Mark II Total Knee Replacement System, published 1985 (Attached as Exhibit G).
Protek F/S Modular Total Knee Replacement System, pp. 1-57, published by Protek in Jan. 1991 (Attached as Exhibit H).
Low Contact Stress Meniscal Bearing Unicompartmental Knee Replacement: Long-Term Evaluation of Cemented and Cementless Results, Journal of Orthopaedic Rheumatology (presented at the 57th Annual American Academy of Orthopaedic Surgeons Meetings, New Orleans, LA, Feb. 11, 1990), Bates No. DEP00004096-DEP00004107.
N.J. Unicompartmental Knee, Dated Sep. 15, 1989, Bates No. DEP00004108-DEP00004116.
Buechel, Frederick F., NJ LCS Unicompartmental Knee System with Porocoat, dated Oct. 24, 1994, Bates No. DEP000004117-DEP00004130.
Buechel, Frederick F. NJ LCS Unicompartmental Knee System with Porocoat, 1994, Bates No. DEP00004131-DEP00004141.
Buechel, Frederick F. NJ LCS Unicompartmental Knee System with Porocoat, 1994, Bates No. DEP00004142-DEP00004152.
Engh, et al., The AMK Total Knee System, Design Rationale and Surgical Procedure, dated 1989, Bates No. DEP00004153-DEP00004201.
Advertising Proteck Mark II PCR Total Knee Replacement System, Journal of Bone and Joint Surgery, 1987, Bates No. DEP00004202-DEP00004230.
Protek, Parts Brochure for Mark II Protek,1987, Bates No. DEP00004231-DEP00004235.

(56) References Cited

OTHER PUBLICATIONS

Chapman, Michael W., *Operative Orthopaedics*, vol. 1, Published by J.B. Lipponcott Co., Philadelphia, dated 1988, Bates No. DEP00004236-DEP00004247.

American Academy of Orthopaedic Surgeons, *Flyer from 57th Annual American Academy of Orthopaedic Surgeons Meeting*, Feb. 13, 1990, Bates No. DEP00004248-DEP00004251.

Crossett et al., *AMK Congruency Instrument System, Surgical Technique*, dated 1997, Bates No. DEP00004252-DEP00004267.

Engh et al., *AMK Surgical Technique*, Bates No. DEP00004268-DEP00004298, dated 1989.

Engh et al., *AMK Surgical Technique*, Bates No. DEP00004299-DEP00004329, dated 1989.

Crenshaw, A.H., *Campbell's Operative Orthopaedics*, 4th Edition, vol. 1, Bates No. DEP00004330-DEP00004333, dated 1963.

Howmedica, *Duraconcept, Design Concepts of the Duracon Total Knee System*, Bates No. DEP00004337-DEP00004337, dated 1993.

Freeman et al., *Total Knee System*, Bates No. DEP00004350-DEP00004361, Published prior to Jun. 7, 1994.

Freeman et al., *F/S Modular Total Knee Replacement System-SICOT*, 90 Edition, Bates No. DEP00004362-DEP00004373, dated 1990.

Buechel, Frederick F., *Howmedica Product Catalog*, Bates No. DEP00004374-DEP00004375, dated 1994.

Massarella, Antony, *Interax Bulletin, No. 6, Tibial Intramedullary Alignment Surgical Technique*, Bates No. DEP00004387-DEP00004390, dated Feb. 23, 1994.

Desjardins et al., *Interax Operative Technique*, Bates No. DEP00004391-DEP00004411, dated 1994.

Desjardins et al., *Interax Total Knee Operative Technique: Monogram Total Knee Instruments*, Bates No. DEP00004412-DEP00004432, dated 1993.

Howmedica, *Interax Tibial IM*, Bates No. DEP00004433-DEP00004433, dated 1994.

Depuy, *LCS Uni PMA Data from FDA Website*, Bates No. DEP00004434-DEP00004434, dated 1991.

Briard et al., *LCS Uni Unicompartmental Knee System with Porocoat*, Bates No. DEP00004452-DEP00004462, dated 1991.

Freeman et al., *Mark II Total Knee Replacement System*, Bates No. DEP00004463-DEP00004492, dated 1985.

Buechel, Frederick F., *NJ LCS Unicompartmental Knee System with Porocoat*, Bates No. DEP00004493-DEP00004503, dated 1994.

Chapman, Michael W. *Operative Orthopaedics*, vol. 3, 2nd Edition, Published by J.B. Lipponcott Co., Bates No. DEP00004504-DEP00004508, dated 1993.

Biomet, *Oxford Meniscal Knee Phase II Unicompartmental Replacement*, Bates No. DEP00004509-DEP00004515, Published prior to Jun. 7, 1994.

Scott et al., *P.F.C. Sigma Unicompartmental Knee System*, Bates No. DEP00004531-DEP00004539, dated 1998.

Freeman et al., *F/S Modular Total Knee Replacement System*, Bates No. DEP00004540-DEP00004596, dated 1990.

Broughton et al., *Unicompartmental Replacement and High Tibial Osteotomy for Osteoarthritis of the Knee*, Journal of Bone and Joint Surgery, vol. 68-B, No. 3, May 1, 1986, pp. 447-452, Bates No. DEP00004752-DEP00004763.

Scott et al., *Unicompartmental and High Tibial Osteotomy for Osteoarthritis of the Knee*, Journal of Bone and Joint Surgery, vol. 63-A, No. 4, Apr. 1, 1981, Bates No. DEP00004764-DEP00004775.

Thornhill, Thomas S., *Unicompartmental Knee Arthroplasty Clinical Orthopaedics and Related Research*, No. 205, Apr. 1, 1986, pp. 121-131, Bates No. DEP00004776-DEP00004791.

Forst et al., *A Special jg for Tibial Resection for the Implantation of GSB-Knee-Prostheses in Problematic cases*, pp. 162-166, dated Jun. 1, 1984, Bates No. DEP00004838-DEP00004842.

Ingillis et al., *Revision Total Knee Replacement Techniques in Orthopedics*, dated Apr. 1, 1990, Bates No. DEP00005583-DEP00005592.

Uvehammer et al., "In Vivo Kinematics of Total Knee Arthroplasty: Concave Versus Posterior-Stabilised Tibial Joint Surface", vol. 82-B, No. 4, May 2000, pp. 499-505.

* cited by examiner

CROSS PIN

FIG. 21A CONDYLAR IMPLANT RESECTION SURFACE

FIG. 21B VIABLE BONE PRESERVED

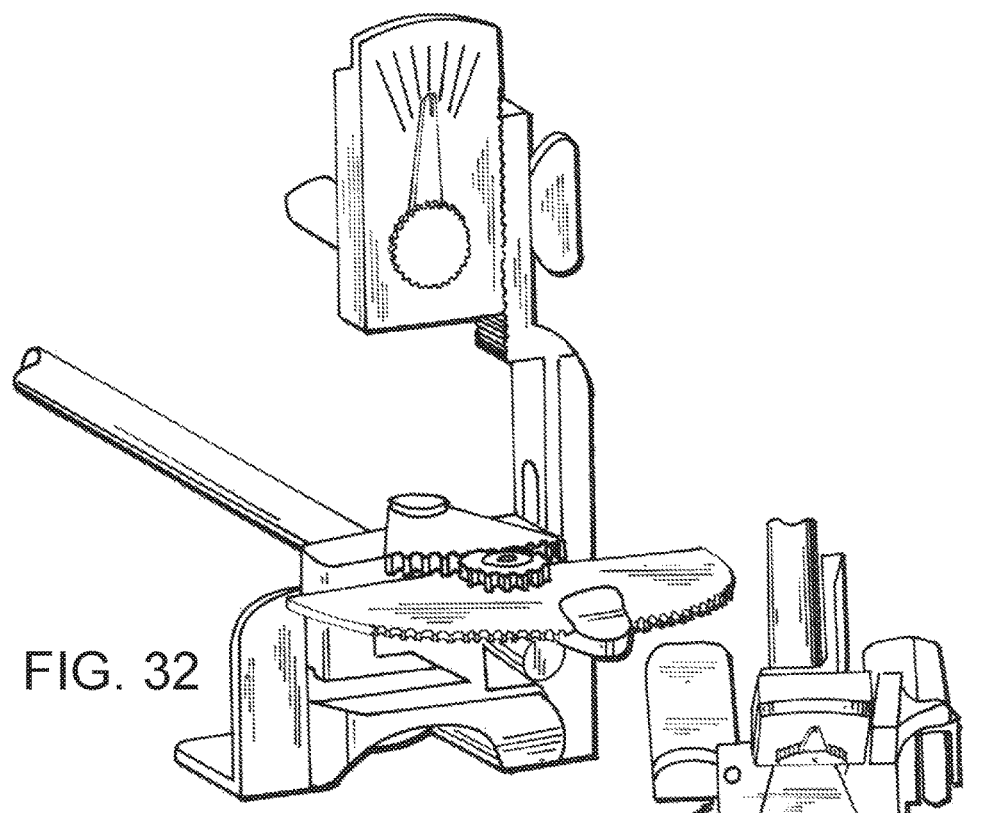
FIG. 32
SOFT TISSUE OR PATELLOFEMORAL ACCOMODATING CONTOUR
FIG. 33
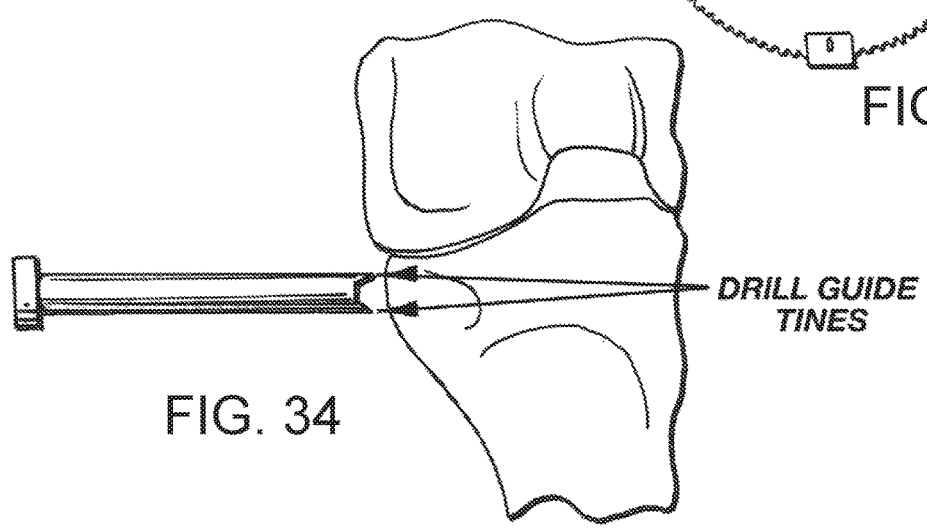
DRILL GUIDE TINES
FIG. 34

DRILL

METHODS AND APPARATUS FOR CONFORMABLE PROSTHETIC IMPLANTS

CLAIM TO PRIORITY

The present invention claims priority to U.S. Provisional Application No. 60/551,631, filed Mar. 8, 2004, entitled, "METHODS AND APPARATUS FOR CONFORMABLE PROSTHETIC IMPLANTS," and claims priority to U.S. Provisional Application No. 60/551,080, filed Mar. 8, 2004, entitled, "METHODS AND APPARATUS FOR PIVOTABLE GUIDE SURFACES FOR ARTHROPLASTY," and claims priority to U.S. Provisional Application No. 60/551,078, filed Mar. 8, 2004, entitled, "METHODS AND APPARATUS FOR MINIMALLY INVASIVE RESECTION," and claims priority to U.S. Provisional Application No. 60/551,096, filed Mar. 8, 2004, entitled, "METHODS AND APPARATUS FOR ENHANCED RETENTION OF PROSTHETIC IMPLANTS," and claims priority to U.S. Provisional Application No. 60/551,307, filed Mar. 8, 2004, entitled, "METHODS AND APPARATUS FOR IMPROVED CUTTING TOOLS FOR RESECTION," and claims priority to U.S. Provisional Application No. 60/551,262, filed Mar. 8, 2004, entitled, "METHODS AND APPARATUS FOR IMPROVED DRILLING AND MILLING TOOLS FOR RESECTION," and claims priority to U.S. Provisional Application No. 60/551,160, filed Mar. 8, 2004, entitled, "METHODS AND APPARATUS FOR IMPROVED PROFILE BASED RESECTION," and is a continuation-in-part of U.S. patent application Ser. No. 11/036,584, filed Jan. 14, 2005, entitled, "METHODS AND APPARATUS FOR PINPLASTY BONE RESECTION," which claims priority to U.S. Provisional Application No. 60/536,320, filed Jan. 14, 2004, and is a continuation-in-part of U.S. patent application Ser. No. 11/049,634, filed Feb. 3, 2005, entitled, "METHODS AND APPARATUS FOR WIREPLASTY BONE RESECTION," which claims priority to U.S. Provisional Application No. 60/540,992, filed Feb. 2, 2004, entitled, "METHODS AND APPARATUS FOR WIREPLASTY BONE RESECTION," the entire disclosures of which are hereby fully incorporated by reference.

BACKGROUND OF THE INVENTION

1. Field of the Invention

This invention generally relates to methods and apparatus for prosthetic implant devices. More particularly, the present invention relates to prosthetic implants for joints that are conformable, preferably both at the time of implant and over the life of the implant.

2. Background Art

The replacement or augmentation of joints with artificial or prosthetic implants is well known in the field of orthopedics. Total knee arthroplasty (TKA) procedures involving the replacement of the knee joint are a good example. U.S. Publ. Appl. 2003/0028196A1 and the PFC RP Knee Replacement manual provide a good background for the techniques and devices used as part of these arthroplasty procedures.

The prosthetic implant devices for use in arthroplasty procedures are typically metallic devices or devices that have a combination of metallic and plastic components. Because of the high loads and strains that these devices must endure for years, almost invariably the design of these prosthetic implant devices relies on the rigid structure and durability of the metallic components to support the loads and strains. While the rigid structure and durability of metallic implants is beneficial in most regards, these features make the fit or interface between the metallic implant and the resected bone surface critical to the long term viability of an implant.

In total knee replacements, for example, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

Over the years, alternatives to metallic prosthetic implants have been proposed. U.S. Pat. Nos. 3,906,550 and 4,693,721 describe a porous metallic fabric for use as a medical implant. U.S. Pat. No. 5,986,169 describes a porous nickel-titanium metal alloy for use as a medical implant. European Publ. Appl. 0 761 242 A1 describes a molded polymer orthopedic implant with a bearing surface formed of a porous metal layer. PCT Publ. Appl. WO 02/34310 A2 describes a shape memory polymer material that is used as a connective tissue replacement material for orthopedic applications. These alternatives have met with little success or acceptance in the orthopedic implant field.

It would be desirable to provide for an orthopedic prosthetic implant that could be implanted more consistently and effectively, yet provided or exceeded the ideal long term wear and stability of current rigid metallic implants.

SUMMARY OF THE INVENTION

The present invention is a biomechanical optimization (BMO) prosthetic implant that utilizes a thin cross-section of metallic material that is conformable. Preferably, the BMO prosthetic implant is conformable both at the time of implant in response to manipulation and fixation by the surgeon, as well as during the life of the implant in response to stresses and loads experienced by the implant and thereby communicated and responded to by living bone tissue. For most metallic alloys, the BMO prosthetic implant will have an effective cross-sectional thickness of 3 mm or less. In one embodiment, the BMO prosthetic implant is provided with one or more fins extending from the fixation surface(s) of the implant which preferably includes retaining structures, such as cross-pinned apertures or T-shaped edge ridge.

In another embodiment of the present invention, the BMO Prosthetic implant is a composite of porous metal or 'Trabecular Metal' bone interface features joined to a thin layer of articular surface material such as cobalt chrome or titanium. This embodiment of the present invention is particularly advantageous as much of the literature available on both Actipore™ (a porous nitinol, which forms a TiNi intermetallic molecule marketed by Biorthex, Inc.) and Trabecular Metal (chemical vapor deposition of tantalum on a porous carbon matrix manufactured by Implex, Inc. and distributed by Zimmer, Inc.) cites that the modulus of elasticity or stiffness of these materials is similar to that of living bone. As a result, the composite structure of the present invention creates an interfacial mechanical environment motivating a highly favorable biological response from the living bone while the articular surface of the present invention will providing for excellent articular function.

Additionally, this embodiment of the present invention may allow for the prosthesis, for example, a femoral or tibial component for use in knee replacement, to have a linear or curvilinear fixation profile of flexible porous material that is substantially thicker (at least 10% thicker, and in one preferred embodiment closer to 500% thicker) than the thickness of the composite articular surface, for intraoperative attachment to condylar cuts having a linear cutting profile of sufficient interfacial area to avoid subsidence of the implant into bone leading to failure. This embodiment can significantly improve the arthroplasty continuum of care for a given patient, as surgeons performing revision procedures will commonly remove necrotic tissue to a depth sufficient to reveal bleeding bone prior to implantation of the revision prostheses. Because these porous metals are capable of accommodating healthy living bone within their interstices, this ensures that this embodiment of the present invention will require a minimum of bony material removal both intraoperatively during primary intervention and intraoperatively during revision intervention. Another alternate embodiment would further have the fin and/or keel and/or crosspin be constructed of such porous material.

The present invention provides for embodiments of prosthetic implant designs facilitating intraoperative and postoperative efficacy and ease of use. The present invention utilizes a number of embodiments of prosthetic implants, or prosthetic implant features to facilitate clinical efficacy of arthroplasty procedures. The overriding objects of the embodiments are to facilitate short and long term fixation of the implant with respect to the bone, enable bone preservation to facilitate ease and efficacy of revision, and/or to take advantage of the natural physiological phenomenon determining bone growth response to load stimuli. Specifically, science is beginning to understand the manner in which bone responds to mechanical stimuli to an extent that allows for at least first order prediction of the clinical performance of prosthetic implants attached to bone. Certain theories regarding bone response to prosthetic implant load transfer to bone are postulated herein and prosthetic implant design embodiments proposed to take advantage of these biomechanical characteristics in facilitating clinical performance are disclosed.

It should be clear that applications of the present invention is not limited to Total Knee Arthroplasty or the other specific applications cited herein, but are rather universally applicable to any form of surgical intervention where the resection of bone is required. These possible applications include, but are not limited to Unicondylar Knee Replacement, Hip Arthroplasty, Ankle Arthroplasty, Spinal Fusion, Osteotomy Procedures (such as High Tibial Osteotomy), ACL or PCL reconstruction, and many others. In essence, any application where an expense, accuracy, precision, soft tissue protection or preservation, minimal incision size or exposure are required or desired for a bone resection and/or prosthetic implantation is a potential application for this technology. In addition, many of the embodiments shown have unique applicability to minimally invasive surgical (MIS) procedures and/or for use in conjunction with Surgical Navigation, Image Guided Surgery, or Computer Aided Surgery systems.

BRIEF DESCRIPTION OF THE DRAWINGS

Other important objects and features of the invention will be apparent from the following detailed description of the invention taken in connection with the accompanying drawings in which:

FIGS. 1-42 show various depictions of embodiments and methods in accordance with alternate embodiments of the present invention.

DETAILED DESCRIPTION OF THE PREFERRED EMBODIMENTS

It should be noted that, in many of the figures, the cut surface created by the cutting tool are shown as having already been completed for the sake of clarity. Similarly, the bones may be shown as being transparent or translucent for the sake of clarity. The guides/pins, cutting tool, bones, and other items disclosed are may be similarly represented for the sake of clarity or brevity.

FIGS. 1 Through 30

FIGS. 1 through 30 generally represent prosthesis and prosthesis fixation feature embodiments of the present invention.

Figure 1:
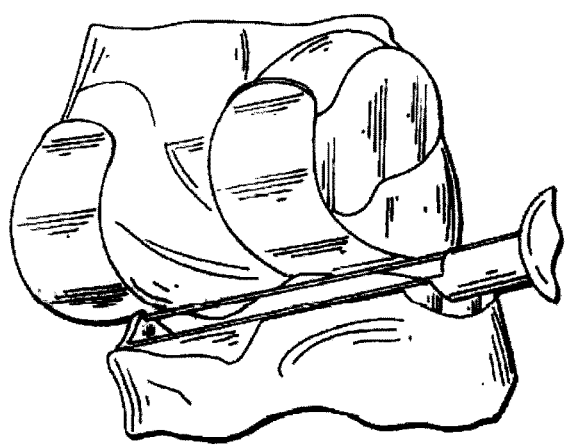
Figure 2:
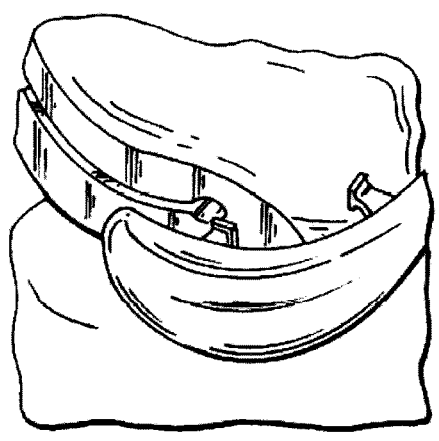
Figure 3:
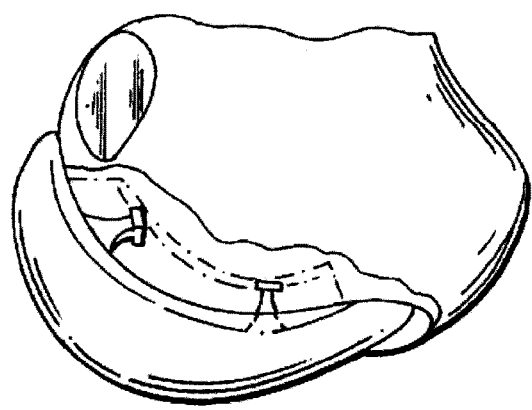
Figure 4:
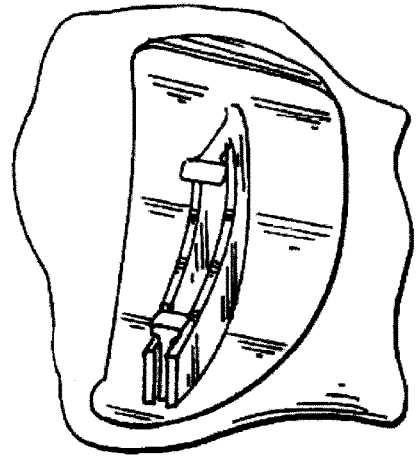
Figure 5:
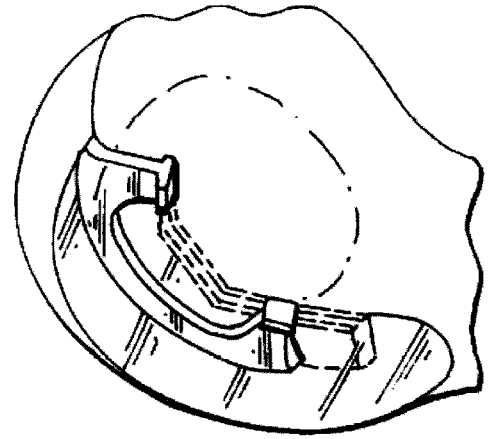
Figure 6:
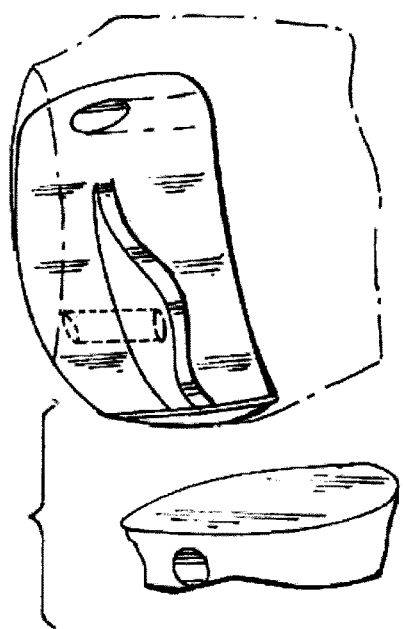
Figure 7:
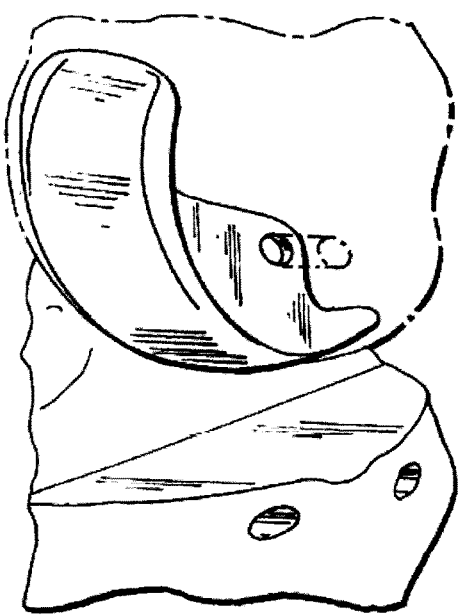

FIGS. 2 through 5 show representations of a tongue in groove fixation feature applied to a Unicondylar femoral component enabling anterior insertion of one tongue element into a 't-slot' style groove formed in bone and a progressively increasing press fit obtained by forcing the implant posteriorly, as is represented in comparing FIGS. 2 and 3. The t-slot feature, or groove, formed in the femur is easily formed by, in one embodiment, providing a trial component possessing a contoured groove and slot for guiding a t-slot cutter along its length. Such a contour groove would be responsible for controlling the depth of the t-slot in the bone with respect to the cut surface to which the implant fixation surface is attached, while the slot in the trial would dictate the mediolateral location of the t-slot style groove. It is preferable to include an aperture in the slot and/or contour groove in the trial component to allow for insertion and plunging of the wider T cutting surfaces prior to sweeping.

Figures 8, 9:
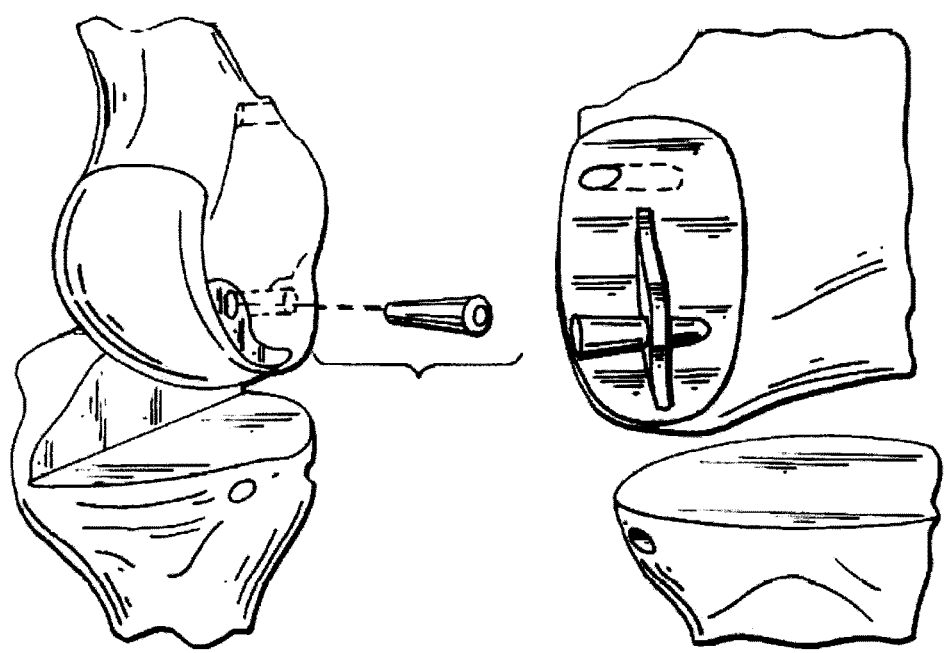

Alternatively, FIGS. 6 through 15 represent combinations of finned and/or crosspinned implants. It should be noted that the AP Fin Profile of the fin may be linear as shown in FIG. 9 (in other words, the fin may be may be planar), or it could be slightly tapered to achieve an interference fit with the walls of the groove as the implant fixation surfaces are forced into contact with the cut surfaces to which they are mated (see FIGS. 10 through 12), or in could be curved as looked at from the viewpoint of FIG. 9 to further provide stability of fixation. Interestingly, the fixation aperture created to fix a cutting guide to the bone could be utilized to cross pin a flange or fin of a femoral prosthesis. It should be noted that although the embodiment shown is a Unicondylar femoral prosthesis, this concept could be applied to tibial, femoral, or patellofemoral prostheses in any application, or in other joint, trauma, spine, or oncology procedures, as is generally represented in FIGS. 23 through 30.

In FIGS. 8 through 15, a tapered pin is used to engage the cross pin hole in the fin of the prosthesis. The tapered pin may be utilized to facilitate a resulting press fit between the pin and the fixation surfaces of the implant and/or ease of introducing the pin into the hole in the fin. The pin could be of any known material, but resorbable materials are especially interesting as they are 'consumed' by the body leaving minimal hardware within the body after a fairly predictable amount of time has passed. PLA/PGA compositions, Tricalcium Phosphate, allograft and autograft bone, bone substitutes, and the aforementioned slurry type compositions may serve well. Additionally, as the apertures shown in FIG. 12 resides close to the natural articular surface and extends through cortical and very robust dense subcondylar bone, a very thin walled coring saw can be used to create the aperture and simultaneously form the crosspin that will be used to facilitate fixation of the implant. Alternatively, bone cement or other liquid or semi-liquid material may be injected into the portals/apertures to achieve intimate interdigitation, and the crosspins optionally inserted thereafter, but prior to complete hardening or curing. Alternatively, the crosspin(s) could be hollow with radially extending holes allowing the pins to be inserted and then have bone cement injected into them and up under the implant. Alternatively, the cross pin could be threaded to engage threads in the fin, or to engage the bone (both for short term stability and to facilitate removal) or both. Alternatively, the crosspin(s) could be formed of bone cement for use in cemented procedures.

These embodiments hold significant promise in both providing for intraoperatively stable cemented or cementless fixation as well as facilitating long term biological ingrowth. It should be noted that the use of multiple holes, pins, and apertures in the prosthesis could be used and that the holes in the bone need not be fixation holes to which guides are attached. It also should be noted that such crosspins used in conjunction with the mating features of the present invention will act to cause the prosthesis to conform to the bone surface about the fixation path of the prosthesis (i.e.; in an anterioposterior direction along the implant fixation surface), but that it may leave something to be desired in its ability to induce similar conformity of implant bone interfaces along the fixation profile of the prosthesis. For clinical applications of embodiments of the present invention where this is a factor, apertures may be present in the implant about more medial or lateral locations that allow the crosspins to mate with said apertures to create the aforementioned intimate fit or conformability in either or both of the ML and AP directions. Also it should be noted the condylar sections, and patellofemoral sections of the implant could be wholly separate, modularly joined, be composed of a dual condylar prosthesis and separate patellofemoral prosthesis, or any combination of the above as generally indicated in FIGS. 23 through 30. Although the bone/implant interface shown is curved in two planes, these concepts apply to implants with 3 planar curved geometry (where the cutting path and cutting profiles of the resected surface geometry and therefore the fixation surface geometry do not remain in two planes through the entirety of the cutting path, or where the cutting path is contained within multiple or single curved surfaces), entirely planar geometries, or anything in between.

Figure 10:
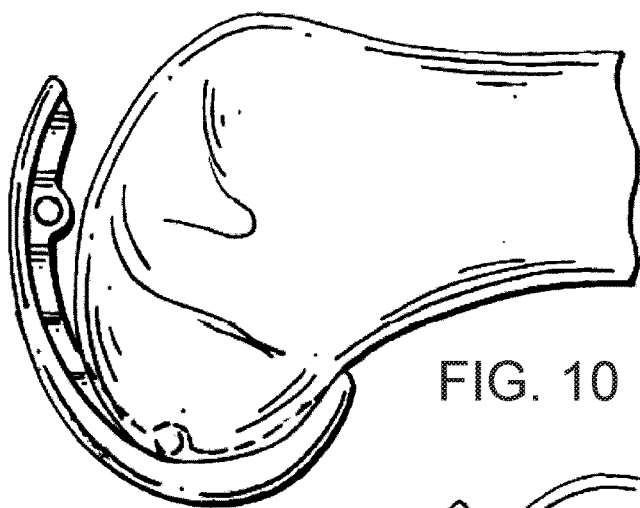
Figure 11:
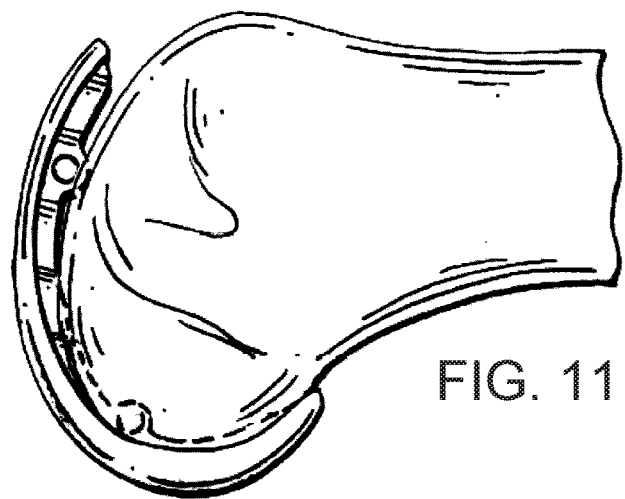
Figure 12:
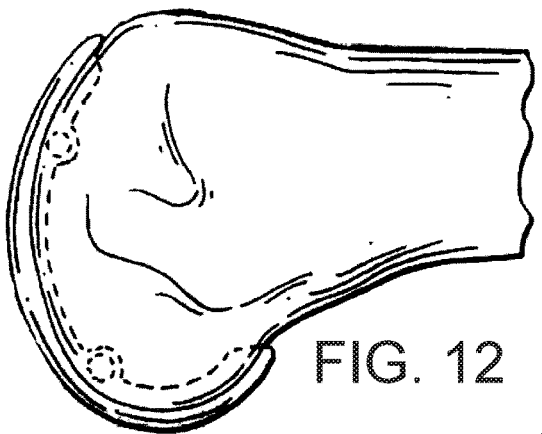
Figure 13:
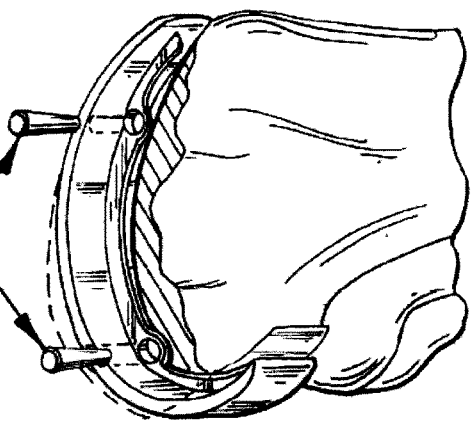
Figure 14:
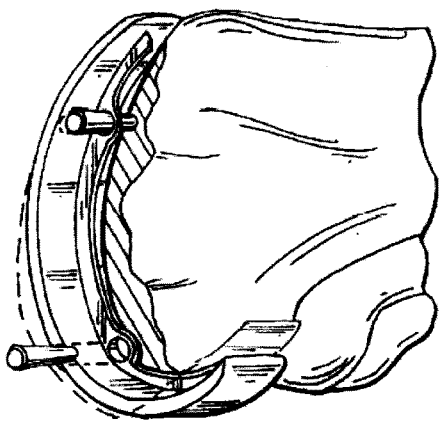
Figure 15:
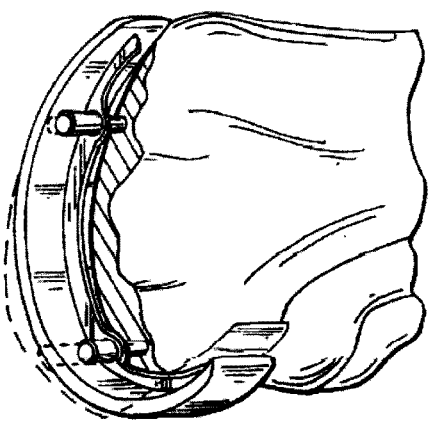
Figure 16:
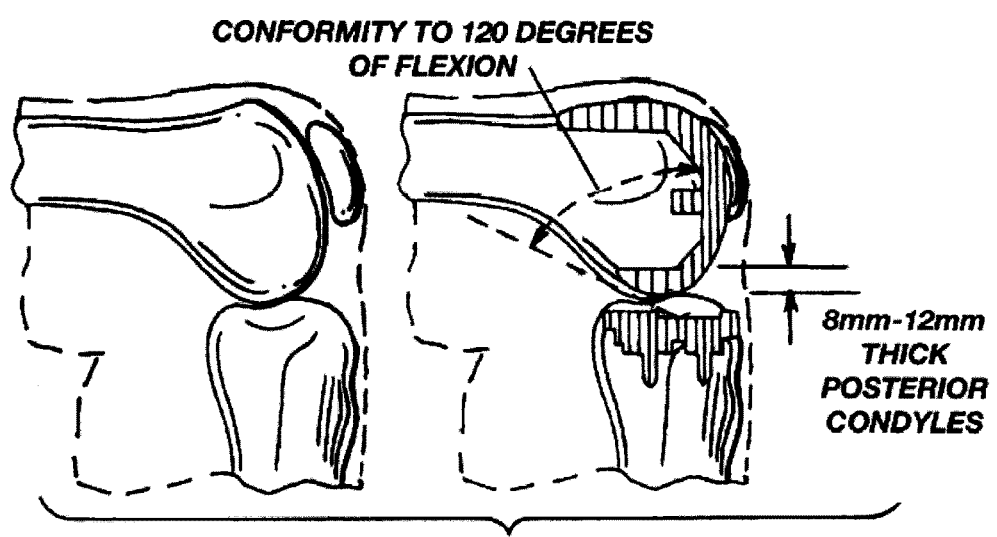

FIGS. 10 through 15 demonstrate another embodiment of the present invention allowing for benefits well above and beyond those of the prior art. This will be referred to herein as a BMO Prosthesis or BMO Cortical type implant (Biomechanical Optimization Prosthesis). This embodiment has several applications. For instance, if the resected surfaces will to vary significantly from the fixation surface geometries, as may be seen in unguided kinematic resection, it may be advantageous to implement fixation surface geometries that can conform to variation in resection geometry. Most implant materials in joint replacement are thought of as being rigid, and that their rigidity is a desirable characteristic for achieving stable fixation. In the case of surface replacement, that is not necessarily the case. Anecdotally, picture a bar of aluminum 2 inches square and 5 inches long—now picture trying to manually bend it. At these dimensions, aluminum is rigid; however, it is obvious that aluminum foil is not so rigid. The point to this is that very thin (less than 3 mm thick, probably closer to a range of 1.5 to 0.01 mm thick) sections of many metals, including implant grade metals and alloys cobalt chrome, titanium, zirconium, and liquid metal, can be processed into very thin forms capable of conforming to variations in the resected surface and yet still have bearing surfaces that are highly polished and provide significant contact area, where desirable, for bearing against the bearing or articular surfaces of the opposing implant. The construct or prosthesis resulting from applying the present invention to a femoral component in Unicondylar knee replacement, for example, may start out being a 1" wide be 3" long strip of 1.5 mm thick material curved in a manner to generally look like the curved cutting path and curved cutting profile of a natural, healthy femur. A process such as Tecotex from Viasys Healthcare of Wilmington, Mass. is used to remove material from the strip down to a nominal thickness of perhaps 0.1 mm thick while leaving multiple protruding 'hooks' (almost like the hook and eye concept of Velcro) emerging from the thin fixation surface to engage the bone. One or more fins can be attached or be made a continuous part of this construct as shown in FIG. 10. During insertion, the anterior most cross pin could lock that portion of the prosthesis in place, then the prosthesis could be wrapped around the remaining, more posteriorly resected surfaces and the posterior cross pin inserted (see FIG. 14). Alternatively, the fins can be located about the periphery of the articular surfaces of the condyle in the form of tabs and the cross pins or screws or tapered dowels, etc. known in the art inserted through holes in the tabs and into bone to fix the cortical implant. The combination of fins and tabs may also be useful. In using the tabs it is critical to keep all features of the implanted device ultralow profile to avoid irritating the surrounding soft tissues (perhaps creating recesses in the bone underlying the tabs would be desirable to allow for a form of countersinking of the tabs and/or the pins or screws or other fixation devices).

The flexibility of the implant in accordance with the present invention allows the implant to conform to the resection surface and the stability of the crosspin fixation would assist in reducing interfacial micromotion known to inhibit bone ingrowth and fixation (this concept could be used with PMMA, but it is also desirable to avoid the tissue necrosis and bone preservation for revision issues associated with the use of bone cement if the patients health/comorbidities/indications allow). This kind of implant has some very interesting clinical benefits beyond simple bone preservation. Given how well this kind of conformable implant impart load to underlying bone, thus avoiding stress shielding, it is possible not only to promote healthy bone ingrowth into and around the interfacial features, but the bearing contact and strains/stresses imparted to the bone could motivate the bone to change its shape (and therefore the shape of the conformable implant also changes over time because of the flexibility) to ideally conform to the tibial component bearing surface such that bearing stresses are carried through the broadest desirable contact area (just like modeling/remodeling in a healthy unmodified joint).

Biomechanically Optimized Implants

The manner in which bone may be motivated to change shape needs to be explained in more detail and is derived from extrapolations of Wolff's Law. One of the modern interpretations of Wolff's Law is that bone 'seeks' a uniform stress state under load through the addition or subtraction of bone material and/or changes in density of bony material. In considering Mattheck's "Axiom Uniform Stress" ("Design in Nature—Learning from Trees" published by Springer-Verlag Berlin, Heidelberg, N.Y., copyright 1998. Mattheck's publications are included herein by reference) which may be paraphrased as "the ideal shape of a given mechanical component is that which results in the component experiencing uniform external stresses during use". Mattheck further provided empirical evidence that the external shape of human and animal bones (and even things like tiger claws and tree limbs) reflect this 'design paradigm' in nature.

The concept of BMO depends on the concept that not only do human bones and articular surfaces in healthy patients seek uniform stresses in bearing, but that bone continues to seek this uniform state despite the pathologies of osteoarthritis. If an implant design is properly designed to allow for localized load transfer to underlying living bone, given that bone will seek an ideal, uniform stress state, it is believed that the bone will adapt its geometry and shape as per the loading it experiences and thus change the shape of the articular surfaces of the BMO implant to reflect ideal or uniform contact stress bearing between the implant articular surfaces. This change in articular geometry would be based on the kinematics of that particular patient's knee joint and the geometry of the articulating surface of the opposing tibial implant (whether it be UHMWPE or any other bearing material) and thereby the stress experienced by living tissues resulting in ideal tibiofemoral articular constraint and conformity. It is believed this biomechanical optimization of articular geometry would yield ideal tibiofemoral contact area and kinematics that are tuned to an individual patient in a manner which standard rigid implants could not hope to match. The debate over what ideal tibiofemoral and patellofemoral prosthesis articular geometries should be has been the topic of heated debate for decades with no clear winner or universally accepted scientific model. The present invention avoids this debate by allowing Mother Nature to cast her vote.

Another interesting embodiment of the present invention is to make both opposing implants BMO Cortical type implants and allow the bone to modify the geometry of both to reach an ideal 'state' for that patient (utilizing Liquid Metal as a metal on metal bearing in this scenario could yield phenomenal results not to mention unheard of bone preservation). The primary objectives of this embodiment of the present invention are to preserve viable bone, to increase prosthesis survival durations, to promote optimal joint kinematics, load transfer, articulation contact areas, and patient satisfaction, reduce intraoperative trauma and patient recovery time, reduce or eliminate proprioceptive compromise, reduce intraoperative time, and generally make the art of joint arthroplasty cheaper, better, and faster in all ways. Further, and perhaps most importantly, the ability to preserve bone to the extent made possible by BMO Cortical type prostheses would enable a given patient who, at younger than normal ages, experiences the debilitating or crippling effects of Osteoarthritis or Post-Traumatic arthritis to be able to be treated by arthroplasty over a period of decades, and a series of revisions that is simply not attainable today given the monolithic nature of conventional implants.

The use of bone morphogenic proteins, bone graft, or other means of promoting or accelerating healing, fixation, and/or ingrowth of devices derived from this concept could be beneficial. Also, application of these inventions to all joint arthroplasty procedures including TKA, hip, ankle, metatarsul, metacarpal, wrist, spine, elbow, shoulder, mandible, or finger or any other joint or bone or bone feature identified in Gray's Anatomy or effected in the aforementioned procedures is likely to provide significant clinical and economic benefit. Implantation of these devices could also be performed via standard surgical approaches or more exotic methods in the art including arthroscopic means or by what has been described as the Transosseous Core approach in the patent literature. Given that properly compacted morselized cancellous bone graft approaches 80% of the Modulus of Elasticity of cortical bone (in compression as per the work of Bonutti, et al), this impaction of graft could actually lend some initial rigidity to the implant. Actually, blood loss from bone surfaces into the joint space has been referred to as problematic in press fit knees, and packing morselized bone graft into living bone and the implant at the bone/implant interface could act as an effective form of tamponade. The process of 'packing' the bone could be affected by simply reducing the joint and allowing the compression across the joint to pack the bone, by injection of osteoslurries into the interfacial area after placement of the implant, or by other currently known methods or those methods to be discovered.

The work of Frost, et al and Lanyon, et al may also have identified several of the characteristics needed for successful replication of bone mechanics. Specifically, it has been identified that living bone tissue experiencing strain states between 50 microstrain to 4,000 microstrain achieves steady state growth balancing out consumption of bone by osteoclast activity and creation of new bone by osteoblast activities. As this strain range is effective in maintaining living tissue, it is likely very beneficial to assume that the healing of interfacial tissues in the postoperative recovery and recuperation periods would be facilitated by ensuring that the fixation apparatus and methods of the present invention be implemented in a manner that maintains the healing interfacial tissues within the aforementioned strain range to facilitate healing and ingrowth of living tissue into the bone-implant interface and avoid the formation of fibrocartilageneous tissue associated with excessive micromotion at this interface (which is known to lead to implant loosening). Fibrocartilagenous tissue is analogous to scar tissue formed by skin after a cut, abrasion, or burn in that it is not generally suited to stable fix a bone-implant interface. Generally, it is known in art of arthroplasty that the formation of fibrocartilagenous tissue at a bone implant interface results in significant pain, sometimes elicited by resulting soft tissue inflammation, for the patient which is something that must be avoided or eliminated for any prosthetic system to be considered successful.

FIGS. 31 through 37

Figure 31:
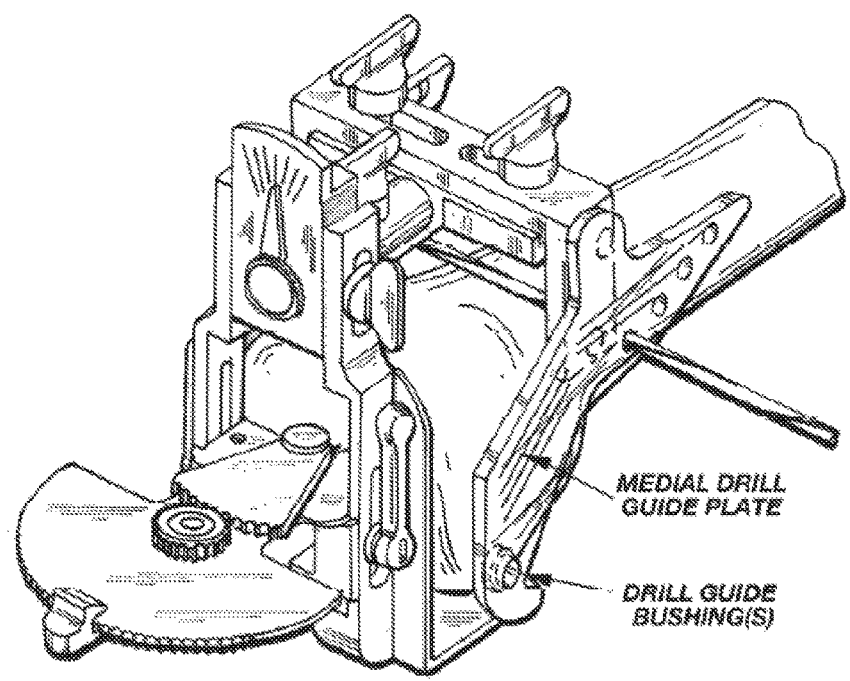

FIGS. 31 through 37 concentrate on alignment guide and/or drill guide techniques. FIG. 31 shows a manually operated alignment guide suitable for use with surgical exposures (it should be noted that surgical navigation sensors could be used to assist in determining final drill guide location and orientation). FIGS. 32 and 33 show an improvement upon the embodiment shown in FIG. 31 for enabling manual alignment guide use in less invasive incisions by providing soft tissue accommodating contours or reliefs. In other words, for a medial parapatellar incision, the alignment guide is configured to allow for appropriate contact and referencing of the distal and posterior femoral condyles, the IM canal (when not relying on an extramedullary reference or inference of the mechanical axis) or IM Rod, the anterior cortex or anterior runout point of a given or proposed implant size (via a stylus not shown), and the epicondylar axis via palpitation or visual reference while the patellar tendon, patella, and/or quadriceps tendon is draped over the lateral side (right side as shown in the figures) of the alignment guide allowing insertion of the guide when the patella is neither everted not fully dislocated as in conventional techniques. It should be noted that initial alignment indicated by reference of the distal femur may be further adjusted in all six degrees of freedom as a fine tuning for final cut location and orientation. This simply calls for the inclusion of additional adjustment of the location and orientation of the crossbar mechanism and/or rotational alignment arm, with respect to the initial reference provide for by contact between the body of the guide and the bone (optionally including the IM Rod), in flexion-extension angulation, varus-valgus angulation (rotational angulation and Anterior-Posterior location are already shown), mediolateral location (represented in this embodiment of the current invention by the cross bar mechanism in FIG. 31 where drill guide mediolateral location is shown as being independently and infinitely adjustable), and proximal-distal location (as shown in FIGS. 31, 32, and 33—it should be noted that this adjustment might be best embodied in an infinitely adjustable slide as opposed to the incrementally adjustable slide shown, and that simple marking would be present indicating the relative movement of the slide with respect to the body). It may be desirable to only utilize only a medial drill guide plate with multiple drill guide bushings to create holes extending partially or completely across the femur depending upon the manner in which the guides are to be connected to the femur.

Figure 35:
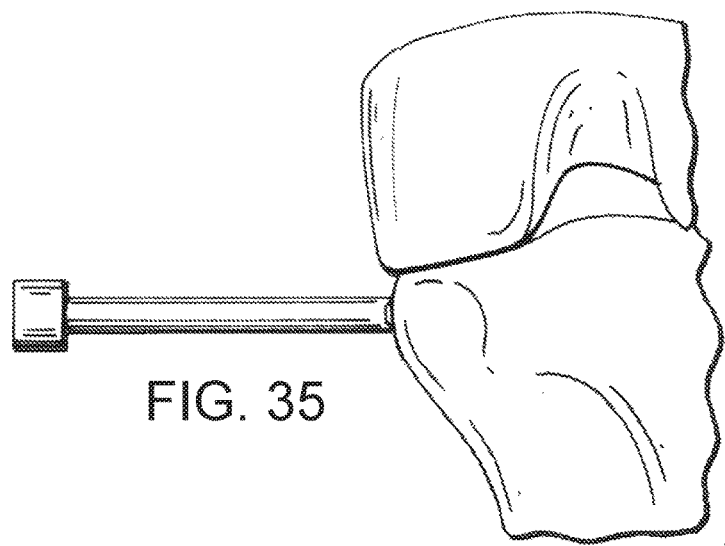
Figure 36:
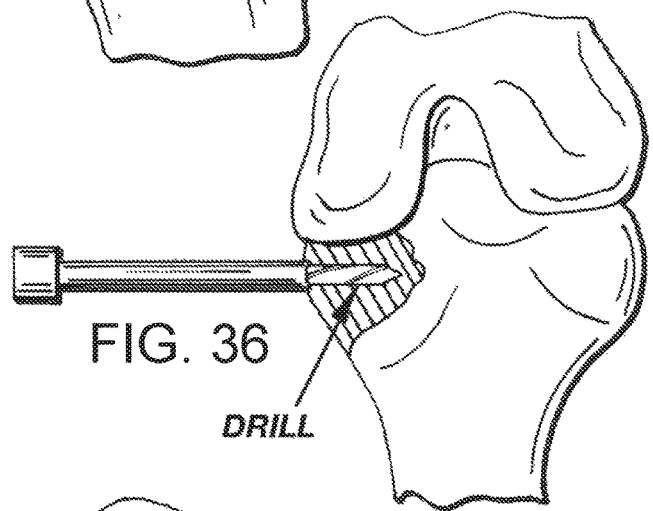
Figure 37:
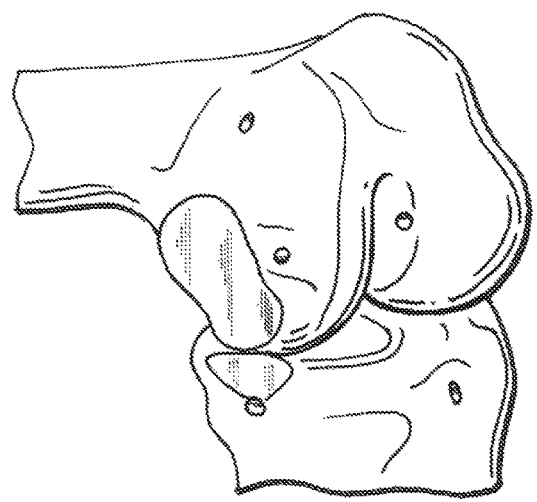

FIGS. 34, 35, and 36 show an alternative alignment/drill guide embodiment of the present invention wherein a cannulated surgically navigated handle/drill guide is used to create fixation apertures in the bone for direct or indirect fixation of a cutting guide. As shown in FIG. 34, it may be advantageous to include tines for penetrating the bone to obtain initial stabilization of the handle in the location and orientation indicated by the surgical navigation system ("Surg Nav"—this term shall be used interchangeably with Computer Aided Surgical System or Image Guided Surgical System throughout this disclosure) prior to extending the drill, represented in FIG. 36, into the bone to create the aperture. An alternate feature to the tines shown could be a smooth but thin walled cylindrical edge of sufficient thinness or sharpness allowing it to cut and penetrate the bone to achieve initial stabilization prior to drilling. It should be noted that the aperture, or hole, thus created could be blind or extended to a specific depth, or optionally extended entirely through the bone and out the furthest side of the bone. Importantly, this process could be utilized transcutaneously through a small stab wound (perhaps 4 mm in length) through the skin to the bone surface, or through a preformed incision through which other instrumentation of the present invention or other devices including the prosthetic implant may be introduced during a procedure. Further, although only one cannulation is shown, a single handle may desirably contain multiple cannulations, some or all of which could be adjustably extended into contact with the bone to reduce any wandering of the drill contacting oblique bone surfaces and improve the precision and accuracy of aperture creation (thus allowing for the creation of apertures in the medial side of the femur, represented in FIG. 37, with a single Surg Nav Handle—Also, the apertures of the drill guide may be configured such that the femoral and tibial apertures shown in FIG. 37 are all created using a single positioning step for the handle). As represented in FIG. 35, there is very little distance over which the drill is cantilevered between its guidance within the cannulation(s) and its point of initial contact with the outer surface of the bone. This aspect of this embodiment of the current invention is critical in preserving the potential accuracy of Surg Nav systems, ie; the navigation system (the computer and the sensors) may be capable of determining appropriate location and orientation to +/−0.5 mm and +/−0.5 degrees, but if the location and/or orientation of the aperture created represents some path of least resistance in bone which is followed by the drill, the resultant location and orientation of cut surfaces, and thereby the location and orientation of the prosthesis attached thereto, will likely be seriously in error. At the end of the day, if the aperture creation step is not carefully controlled, you will have a very expensive alignment system whose stated purpose is to increase reproducibility, and whose method of implementation compromises this stated purpose.

It should also be noted that the methods described herein are applicable to the methods demonstrated in Provisional Patent Application Ser. No. 60/536,320 "Methods and Apparatus for Pinplasty Bone Resection", and Provisional Patent Application Ser. No. 60/540,992, entitled "Methods and Apparatus for Wireplasty Bone Resection."

Figure 38A:
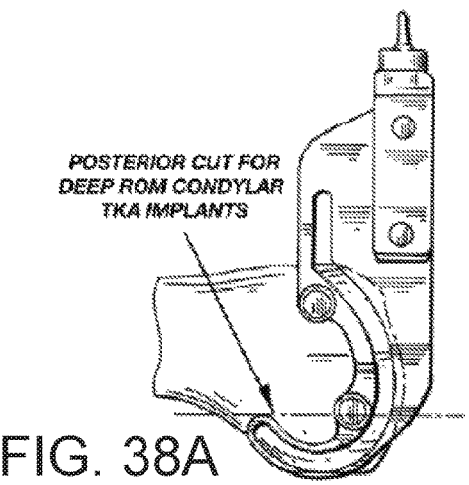
Figure 38B:
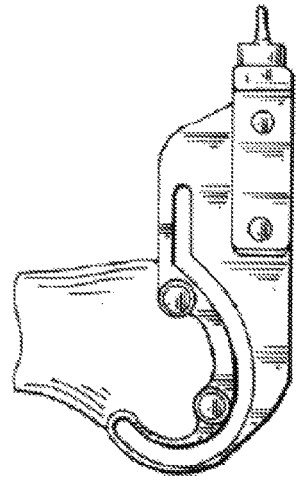
Figure 39:
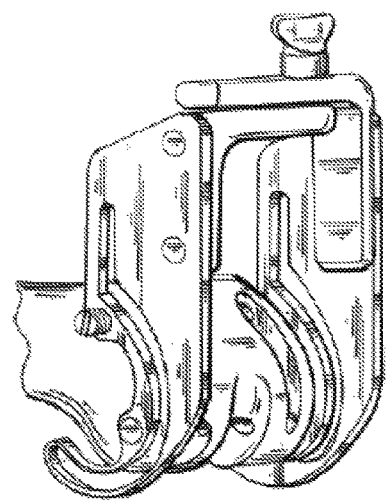

FIGS. 38A through 39, represent embodiments of the present invention for use in bone preserving resection techniques. As noted in FIGS. 38A-38B, and 19-21, a significant amount of viable bone tissue may be preserved while maintaining all functional paradigms of conventional TKA while improving articular conformity in the deepest ranges of flexion. It is of particular interest to note that this is especially applicable in improving the results of conventional Unicondylar implant performance, as the current state of the art makes minimal planar posterior cuts which prohibit articular conformity in deep flexion. This is something of a 'catch 22' as Unicondylar replacement is most often implemented in younger patients whom place higher functional demands, specifically they bend their knees more deeply than their older counterparts, on their implants, yet in an effort to preserve bone for revision, most unicondylar replacements don't possess nearly the range of motion with conformity necessary. Thus a Unicondylar design incorporating deep flexion articular surfaces (as shown in FIG. 19) and corresponding fixation surfaces could simultaneously offer articular conformity and bone preservation for these younger or more physically active patients who are more likely to demand higher performance and require revision to TKA.

Figure 17:
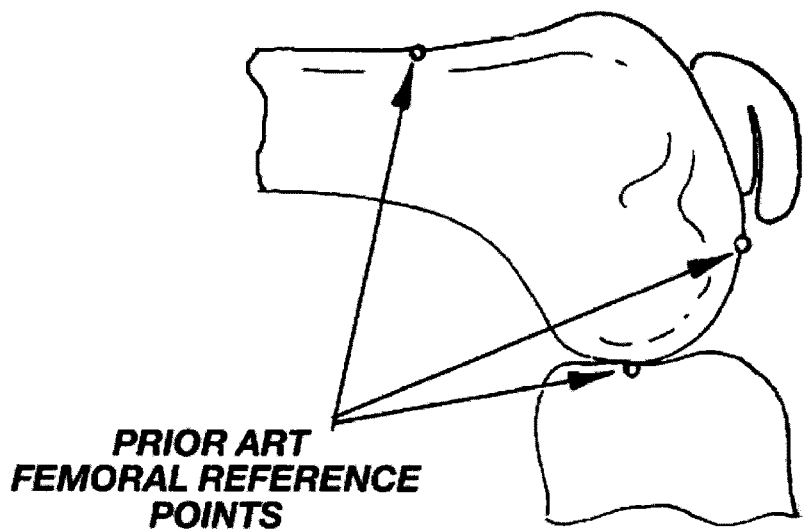
Figure 18:
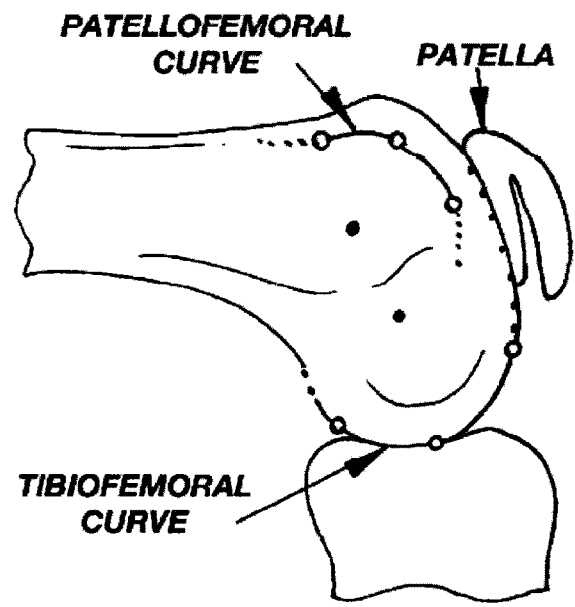
Figure 19:
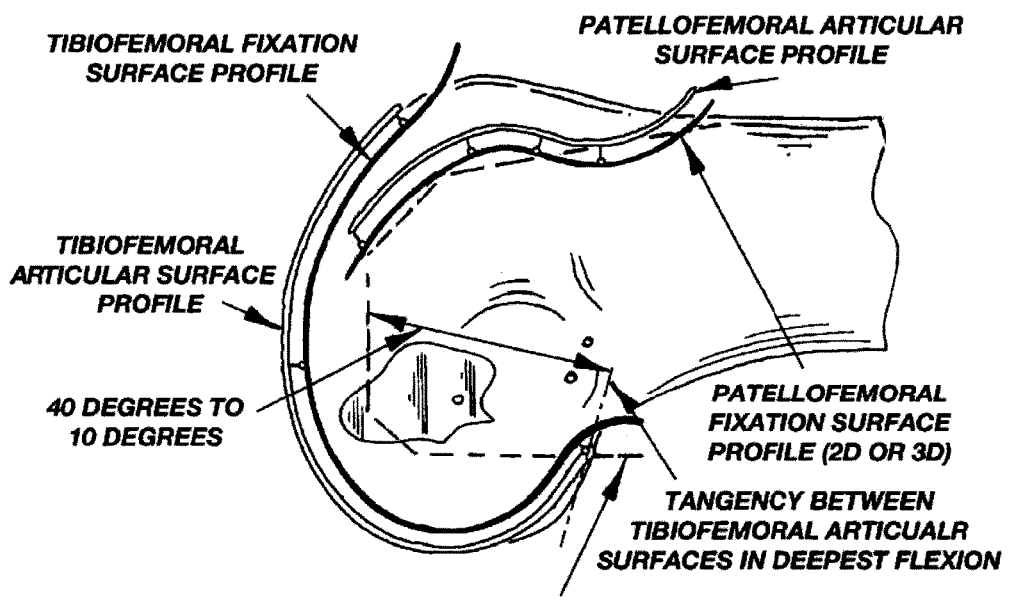
Figures 20, 21, 21C:
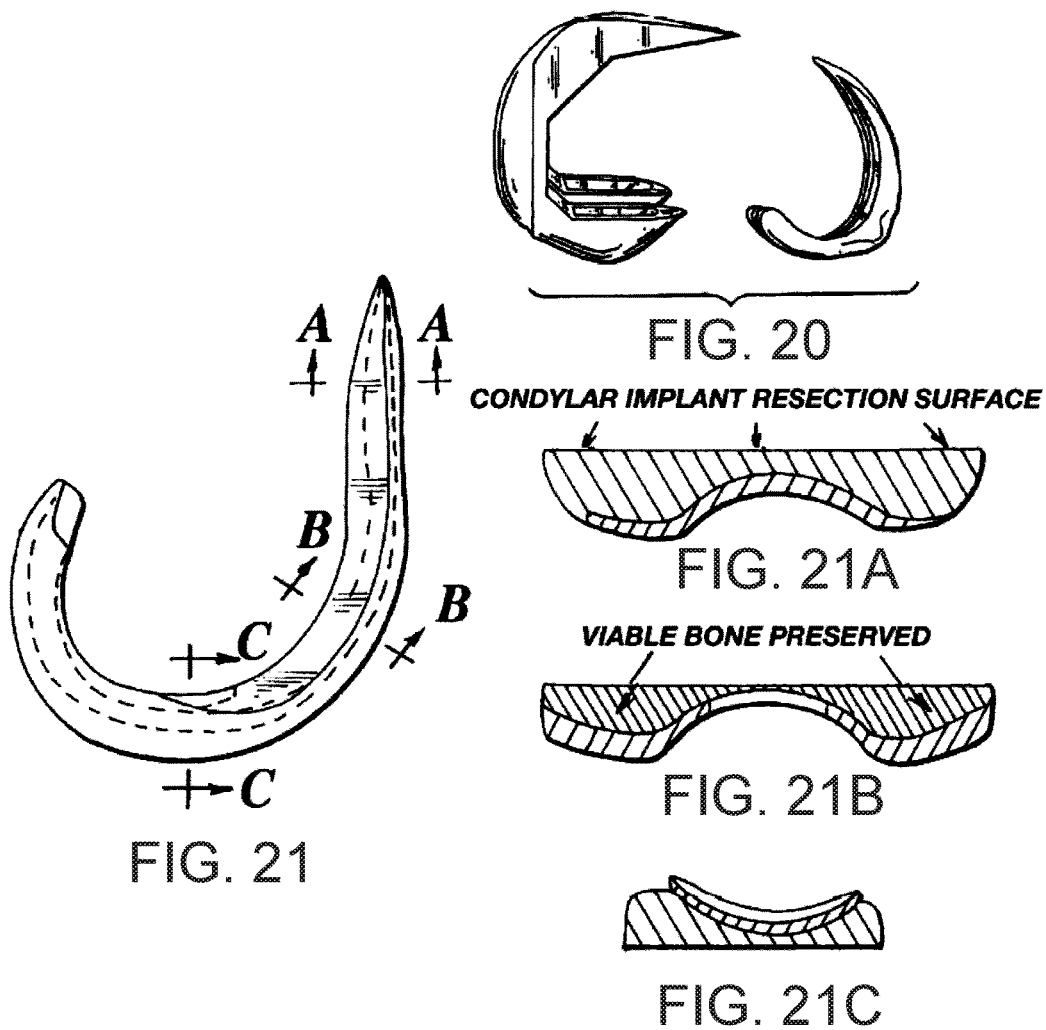
Figure 22:
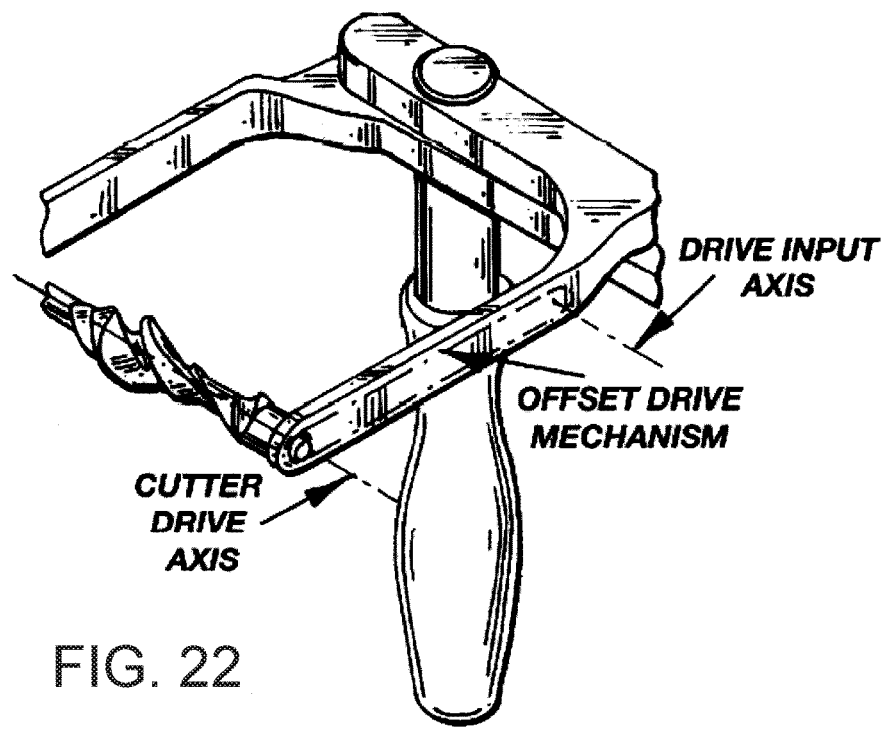
Figure 23:
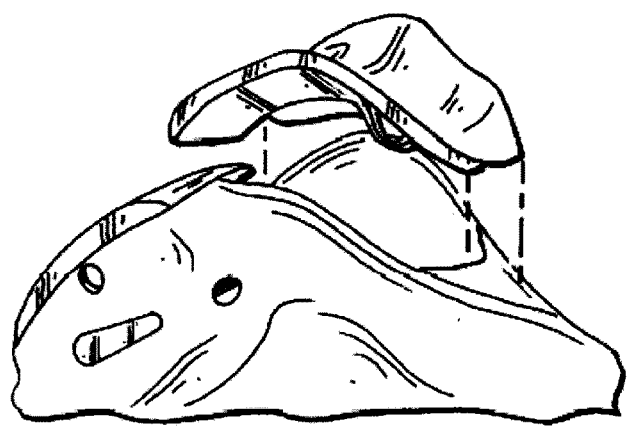
Figure 24:
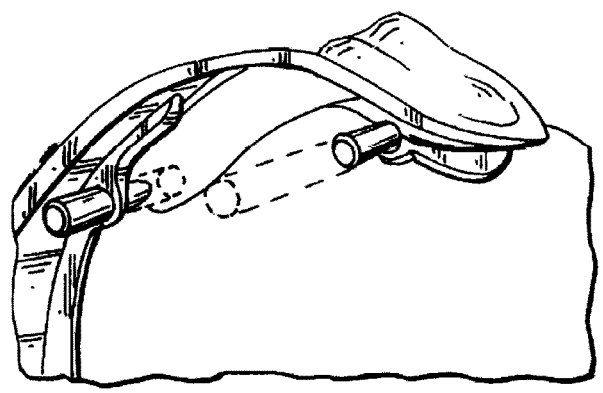
Figure 25:
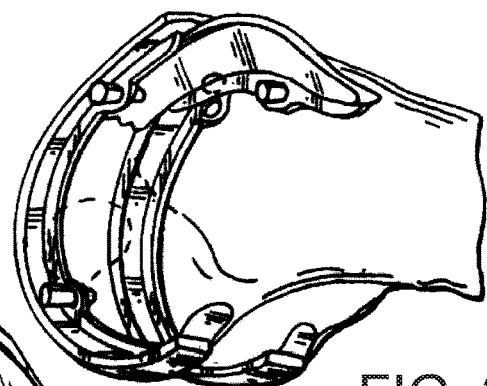

FIGS. 17 through 19 are an embodiment of the present invention that may prove to be a very usefully alternative to conventional rectilinear based referencing techniques. In essence, conventional alignment techniques, once having established appropriate flexion extension angulation and varus valgus angulation of desired implant location, reference the anterior cortex, distal most femoral condylar surface, and posterior most condylar surface (indicated in FIG. 17 by stars) to dictate the anterior posterior location, proximal distal location (otherwise known as distal resection depth), and appropriate implant size in determining the 'perfect' location and orientation for the appropriately sized implant (mediolateral location is normally 'eyeballed' by comparison of some visual reference of the mediolateral border surrounding the distal cut surface and some form of visual guide reference). These conventional techniques fail to directly reference the distinctly different anatomic bone features that dictate the performance of distinctly separate, but functionally interrelated, kinematic phenomena, and they also attempt to reference curvilinear articular surfaces by way of rectilinear approximations. The embodiment of the present invention is an alternative alignment technique with an object to overcome the errors inherent in prior art. As shown in FIG. 18, the femur possesses two distinct kinematic features and functions that lend themselves to physical referencing; the patellofemoral articular surface and the tibiofemoral articular surfaces, both of which are curved, more specifically these surfaces represent logarithmic curves. The one codependency between the two articular functions, and therefore any geometric approximation made of them in referencing, is that they must allow for smooth kinematically appropriate articulation of the patella as it passes from its articulation with the trochlear groove to its articulation with intercondylar surfaces between the femoral condyles. Thus, knowing that three points define an arc and may be used to approximate a curve or sections of a curve, what is proposed is to use a referencing device which contacts at least one femoral condyle at three points to determine both an approximation of arc radius and centerpoint location, while independently or simultaneously referencing the trochlear groove at three points to determine both an approximation of arc radius and centerpoint location. The referencing system would further need to provide for the need of the articular surfaces of the trochlear articular surfaces to smoothly transition to those of the intercondylar surfaces. Armed with this information, a surgeon may most appropriately determine appropriate implant location and orientation.

Figure 26:
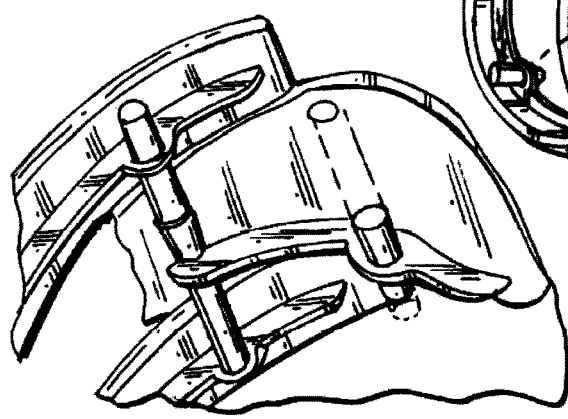
Figure 27:
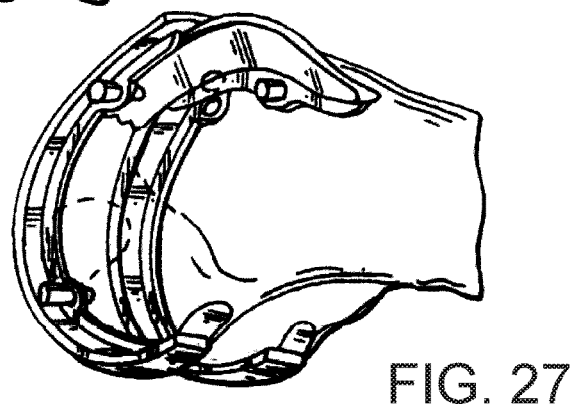
Figure 28:
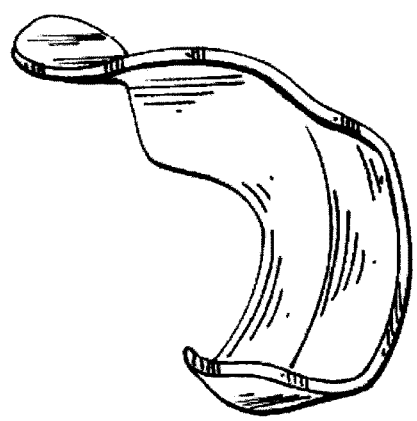
Figure 29:
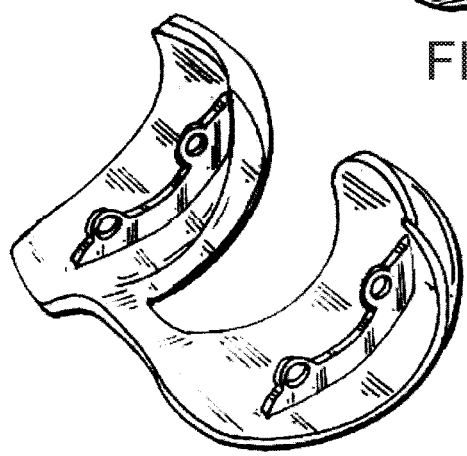
Figure 30:
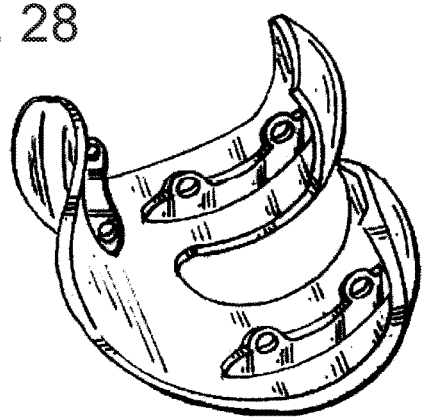

This embodiment of the present invention is especially useful in determining the proper location, orientation, and implant size for the modular tricompartment components shown in FIGS. 23 through 27, the non-modular implants shown in FIGS. 28 through 30, and standard implants where the appropriate size, location, and orientation would be determined by that which best mimics existing articular bone surfaces thus resulting in optimal postoperative kinematic function. FIG. 26 represents one method of fixing the patellofemoral implant with respect to the condylar implant(s) so as to maintain smooth transitional articulation. It should be noted that this crosspin method of interconnecting the separate components could be augmented by tongue and groove interlocking between the medial side of the condylar component shown and the lateral side of the patellofemoral component shown. What is critical is that the transition between the patellofemoral component and the condylar component surfaces responsible for patellofemoral articulation are and remain tangent at least one point.

The following patents and patent applications describing various surgical navigation system and alignment and cutting guide systems that are beneficially utilized in whole or in part with the embodiments of the present invention and are herein incorporated by reference: U.S. 2004/0122436, U.S. 2003/0069591, U.S. 2004/0039396, U.S. 2004/0153083, U.S. Pat. No. 5,810,827, U.S. Pat. No. 6,595,997, U.S. 2003/0069585, U.S. 2003/0028196, JP74214-2002, U.S. 2003/0208122, U.S. Pat. No. 6,725,080, U.S. 2004/0122305, U.S. Pat. No. 6,685,711, U.S. 2004/0153085, U.S. 2004/0152970, U.S. Pat. No. 6,694,168, WO04100758, WO04070580, WO04069036, U.S. Pat. No. 5,799,055, U.S. Pat. No. 6,236,875, U.S. Pat. No. 6,285,902, U.S. Pat. No. 6,340,363, U.S. Pat. No. 6,348,058, U.S. Pat. No. 6,430,434, U.S. Pat. No. 6,470,207, U.S. Pat. No. 6,477,400, U.S. Pat. No. 6,491,699, U.S. Pat. No. 6,697,664, U.S. Pat. No. 6,701,174, U.S. Pat. No. 6,711,432, U.S. Pat. No. 6,725,080, U.S. Pat. No. 6,796,988, and U.S. Pat. No. 6,827,723. Image guidance techniques typically involve acquiring preoperative images of the relevant anatomical structures and generating a data base which represents a three dimensional model of the anatomical structures. The relevant surgical instruments typically have a known and fixed geometry which is also defined preoperatively. During the surgical procedure, the position of the instrument being used is registered with the anatomical coordinate system and a graphical display showing the relative positions of the tool and anatomical structure may be computed in real time and displayed for the surgeon to assist the surgeon in properly positioning and manipulating the surgical instrument with respect to the relevant anatomical structure.

As is known in the art, the relevant dimensional data concerning an anatomical structure of interest, e.g., a femur, may be determined using data acquired from images of the anatomical structure to generate a data base representing a model of the anatomical structure. The model of the anatomical structure may be a three dimensional model which is developed by acquiring a series of two dimensional images of the anatomical structure. Alternatively, the model of the anatomical structure may be a set of two dimensional images having known spatial relationships or other data structure which can be used to convey information concerning the three dimensional form of the anatomical structure. The model of the anatomical structure may then be used to generate displays of the anatomical structure from various perspectives for preoperative planning purposes and intraoperative navigational purposes. A variety of technologies which may be employed to generate such a model of an anatomical structure are well known in the art and include computed tomography (CT), magnetic resonance imaging (MRI), positron emission tomography (PET), ultrasound scanning and fluoroscopic imaging technologies.

In one embodiment, the present invention contemplates a computer-based method of generating a surgical plan comprising reading digital data associated with a 3D (three-dimensional) model of a patient's bone, wherein the digital data resides in a memory in a computer; and generating a surgical plan for the patient's bone based on an analysis of the digital data associated with the 3D model. A surgical planner/simulator module in the computer assisted orthopedic surgery planner software makes a detailed surgical plan using realistic 3D computer graphics and animation. The simulated surgical plan may be viewed on a display seen of a personal computer. The planner module may also generate a pre-surgery report documenting various aspects of the bone surgery.

Figure 40:
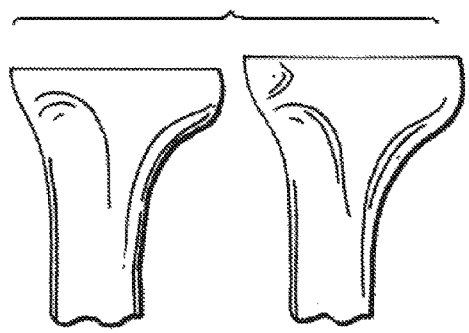
Figure 41:
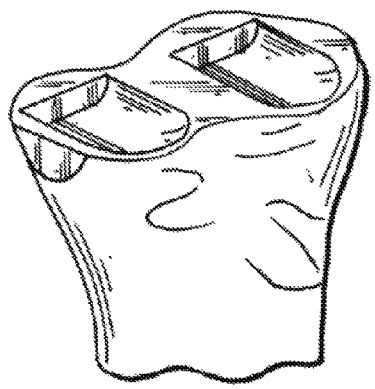
Figure 42:
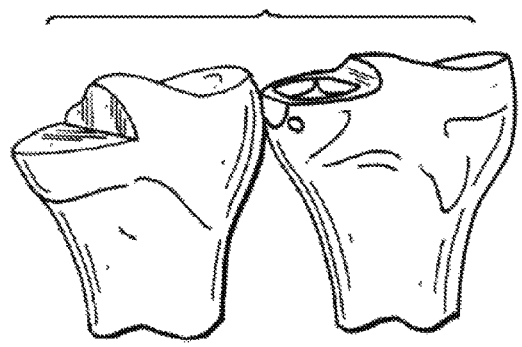

FIGS. 40 through 42

An implant design embodying fixation geometries for mating with such tibial cut surfaces as are shown in FIGS. 40 through 42 is highly desirable. In one embodiment of such a tibial prosthesis design, the fixation surfaces would be intended to mate, directly or indirectly, with cut surfaces represented in FIGS. 41 and/or 42 (the tibia in the right side of the FIG. 42). In essence, the tibial implant would possess a planar or gently curvilinear 'rim' for contacting the 'cortical skim cut' surface (represented in FIG. 40), and convex fixation surfaces for direct or indirect fixation to the concave tibial cuts represented in FIGS. 41 and 42. Direct fixation to such surfaces could be achieved by high precision resection of both the cortical rim, for attachment of the rim of the tibial prosthesis, and the concave surface(s), for intimate apposition to the convex implant surfaces. Such fixation, specifically of the concave bone cuts to the convex implant surfaces, could be achieved by way of an interference fit between the cuts and the implant along one axis (for instance, a front to back—AP—axis or direction), or along two axes (for instance, AP and Side to Side—ML—axes), or circumferentially (in other words a bit like a pin of a given diameter being forced into a hole of a lesser diameter), or both circumferentially and along an axis at roughly a 90 degree angle or normal to the skim cut surface when viewed in one or two orthogonal planes (an "up and down axis" or superior-inferior or proximal distal direction). It should be noted that an interference fit in a roughly superior-inferior direction may call for a textured surface on the bottom most surface of the convex fixation surfaces presenting a small surface area of contact at initial contact with the bottom of the concave cut to allow the implant to compact a reduced area of cancellous bone as the implant is impacted in a superior to inferior direction until it reaches its desired superior-inferior location and/or contact between the rim of the implant and the skim cut of the cortices. As compared to previous methods of achieving implant fixation, these embodiments of the present invention yield superior stability of implant fixation to bone to an extent reminiscent of the difference between riding a horse wearing a deeply dished saddle and riding a very sweaty horse bareback.

An alternative fixation paradigm allows for less intensive demands for the precision of the fit between concave tibial cuts and convex fixation surface. In essence, the concave surface may be 'excavated' in any desired manner (such as the Cutting Trials which cut the proximal tibia while the tibia is moved through at least a portion of its range of motion about the femur), and a morselized or granular osteobiological substance, perhaps tricalcium phosphate, HATCP, or other substances generally described as 'bone substitutes' or autograft or allograft cancellous or cortical bone (it would be very useful to use the bone which was removed from the tibia or other patient bone during the creation of the cut(s) in that it is readily available and completely avoids the issues of disease transmission or immune response), is then impacted into the concave surface using a 'form' to create a surface of impact material (referred to herein as the "Impacted Surface") of specific shape and location/orientation with respect to the cortical skim cut and/or the tibia or femur. This form is beneficially shaped in a manner related to the shape of the convex implant fixation surface shape so as to create a specific geometric relationship between the implant fixation surfaces and the Impacted Surface geometry. In one embodiment of the present invention, the fit between the implant and the Impacted Surface would be an interference fit or press fit. As properly impacted morselized cancellous bone is known to achieve stiffnesses (or modulus of elasticity) that approach as much as 80% of the stiffness of cortical bone in compression, robust intraoperative fixation may be achieved in this manner. In another embodiment, the fit would leave a significant gap, perhaps 0.2 mm to 4.0 mm in width, between portions or all of the convex fixation surfaces of the implant and the convex cut(s), into which bone cement or other substance would then be injected or impacted achieving interdigitation with both the surfaces of the prosthesis and the material of the Impacted Surface. This results in what could be described as composite interface of both biologically active and non-living but structurally robust materials to facilitate both immediate intraoperative stability by way of simple mechanics and long term stability by way of improved load transfer between the implant and the bone eliciting a beneficial biological response by the bone to said loading resulting in intimate and mechanically robust apposition between the composite interface and living tissue over time. It should be noted that such a method prevents excessive micromotion or strain at the interface between the implant (and/or the composite interface) and living tissue during the postoperative healing process, which, in essence, gives the bone a chance to further stabilize its fixation to the implant by way of bone modeling or remodeling in response to load transfer. Specifically, it is highly beneficial to maintain the strain state within living bone at and/or beneath and/or in the general vicinity of the bone implant interface within a range of 50 microstrain to 4000 microstrain so as to elicit the formation of bone tissue at and around the interface—strain levels in excess of 4000 microstrain or less than 50 microstrain are very likely to elicit the formation of fibrocartilagenous tissues at the interface which may lead to aseptic loosening of the implant. In the embodiment where the bone cement is injected, a small hole located at or beneath the skim cut allows for the injection of the material beneath the implant to achieve intimate and controlled interdigitation. Alternatively, the implant could be seated 'over' the freshly cut concave surfaces, and a slurry of biologically active and/or mechanically robust material(s) injected into the gaps between the implant and the bone under controlled pressure. Injection could be achieved via the portal shown in FIG. 42. Such a slurry may comprise a mixture of substances such as morselized patient bone and bone cement, but alternative or additional materials including bone substitutes, osteobiologicals such as bone morphogenic proteins, antibiotics, or even living cells such as T cells known to promote postoperative healing and long term implant fixation. Beneficially, a fin feature may be added to these embodiments to facilitate additional mechanical stability, and said stem feature could beneficially possess an aperture for cross-pin fixation as described below for use in conjunction with the cross pins represented in FIG. 14.

Importantly, it is an objective of the embodiments of the present invention to preserve living, structurally viable bone tissue to facilitate the efficacy of any subsequent revision procedures. Further, the location and geometry of the concave tibial cut allows for the use of a bearing insert (conventionally made of materials such as polyethylene or other materials capable of 'whetting' or mimicking the benefits of 'whetting' during bearing contact; mimicking constituting, in one embodiment, the absence or mitigation of wear debris generation despite the application of significant bearing forces, in TKA in excess of 200 lbs and often as much as 500 lbs or more) whose 'underside' is convexly shaped to mate with a concavely shaped mating or accommodating surface in the upper surface of the tibial implant or 'baseplate' as it is sometimes referred to. This allows for a tibial insert(s) whose thickness, in the areas beneath where the femoral implant bears against the tibial insert, may be equal to or greater than those insert thicknesses used in the past (those associated with predominantly planar tibial cuts) while require removal of significantly less structurally viable bone from the cortical rim of the proximal tibia than past efforts. Determination of the geometry and location of the baseplate's concave surface and therefore the areas of greatest insert or bearing surface are easily determined by analysis of the wear patterns of retrieved tibial inserts. These embodiments of the present inventions also facilitate significant clinical benefits when applied to meniscal or rotating platform TKA designs as a high degree of conformity may be achieved while constraint is mitigated while preserving significantly more bone than prior art devices. Further, the reproducibility of the methods and apparatus described herein enable independent attachment of single compartment implants to bone to achieve Unicondylar, Bicondylar, Bicondylar and Patellofemoral, or Unicompartmental and Patellofemoral replacement of damaged bone surfaces while achieving the objectives of bone preservation, robust immediate and short and long term fixation, reproducibility of implant fixation and resulting location and orientation, and intraoperative ease of use.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. An implantable orthopedic prosthesis for implantation on a long bone of a knee joint during a knee arthroplasty procedure, comprising:
    an implant body formed of a metallic material and having a fixation surface configured to face a resected surface on the long bone and an articulation surface adapted to articulate with respect to a second long bone of the knee joint through a range of motion of greater than 45 degrees, and
    the implant body having a mediolateral cross-sectional shape at least partially defined by the fixation surface and the articulation surface that generally corresponds to a shape of tissue being replaced by the implant body, the implant body including at least first and second spaced apart fixation features, the first and second fixation features adapted to be sequentially affixed to the long bone, and
    wherein the fixation surface has a preoperative fixation path that is adapted to diverge anteriorly from a cutting path of the resected surface when a posterior portion of the fixation surface is in contact with and fixed to a corresponding posterior portion of the resected surface with the first fixation feature, and the implant is sufficiently flexible to enable a surgeon to force the implant to deform so as to cause an intraoperative fixation path of the fixation surface to substantially match the cutting path prior to fixing an anterior portion of the fixation surface to the bone with the second fixation feature.

2. The implantable orthopedic prosthesis of claim 1, wherein the first and second fixation features each comprise a projection structure extending inwardly from the fixation surface of the implant body, the projection structure being adapted to face surfaces of a corresponding cavity created in the bone.

3. The implantable orthopedic prosthesis of claim 2, further comprising:
    means for laterally retaining each projection structure such that a preload force is exerted on the implant body that causes the implant body to be biased against the bone in a direction generally perpendicular to at least a portion of the fixation surface.

4. The implantable orthopedic prosthesis of claim 3, wherein the means for laterally retaining comprises at least one retention aperture defined in the at least one projection structure and a corresponding cross pin adapted to mate with the at least one retention aperture.

5. The implantable orthopedic prosthesis of claim 2, wherein the projection structure is comprised of a porous metal capable of lateral fluid communication between generally opposing sides of the projection structure to permit tissue in growth through the projection structure post operatively.

6. The implantable orthopedic prosthesis of claim 2, wherein a depth of the projection structure extends inwardly from the fixation surface of the implant body a distance at least as large as a depth of the implant body.

7. The implantable orthopedic prosthesis of claim 3, wherein the preload force induces compressive strains in the fixation surface of the implant body along an axis normal to an axis normal to the fixation surface of the implant.

8. The implant of claim 3, wherein the means for laterally retaining the each projection structure such that a preload force is exerted on the implant body is effected by the advancement of one of a cross pin, a threaded pin, a tapered pin, bone cement, and a flowable material into an aperture formed in bone and into contact with the projection structure after the implant has been brought into contact with the bone.

9. The implantable orthopedic prosthesis of claim 4, wherein the cross pin is cannulated to allow injection of flowable material through the pin and into bone generally adjacent the retention aperture, wherein the flowable material is selected from the group consisting of bone cement and flowable slurry.

10. The implantable orthopedic prosthesis of claim 4, wherein the means for laterally retaining comprises at least two retention apertures defined in the at least one fin structure and a corresponding cross pin adapted to mate with each retention aperture.

11. The implantable orthopedic prosthesis of claim 1, wherein at least one fixation feature includes an aperture through which flowable material is injected to form at least a portion of a lateral retention feature in bone.

12. The implantable orthopedic prosthesis of claim 1, wherein the articulation surface changes shape in response to changes in the shape of the bone after implantation.

13. The implant of claim 1, wherein the implant body is sufficiently flexible to allow the fixation surface to conform to the resected surface during an expected life cycle of the implantable prosthesis in response to stresses and loads experienced by the implant body.

14. An implantable orthopedic prosthesis for implantation on a resected surface of a bone of a patient during an arthroplasty procedure, the implantable prosthesis comprising:
    an implant body having a fixation surface facing the bone and an articulation surface adapted to articulate with respect to a second bone of a knee joint through a range of motion of greater than 45 degrees, the implant body being a composite of a porous bulk construct that forms the fixation surface and a thin layer of a material selected from the group consisting of a metallic material or a ceramic material having a smooth bearing surface that forms the articulation surface, wherein the porous bulk construct is substantially thicker than a surface coating and wherein the fixation surface has a preoperative fixation path that is adapted to diverge from a cutting path of the resected surface when one of a posterior portion or an anterior portion of the fixation surface is in contact with a corresponding posterior or anterior portion of the resected surface and the implant is sufficiently flexible to enable a surgeon to force the implant to deform the other of the posterior portion or the anterior portion to cause the preoperative fixation path to change shape to substantially match the cutting path.

15. The implantable orthopedic prosthesis of claim 14, wherein the implant body further comprises: at least one projection structure extending inwardly from the fixation surface of the implant body relative to the bone, the projection structure being adapted to interface with a corresponding cavity created in the bone.

16. The implantable orthopedic prosthesis of claim 15, further comprising: means for laterally retaining the at least one projection structure such that a preload force is exerted on the implant body biasing the fixation surface of the implant body against the bone.

17. The implantable orthopedic prosthesis of claim 16, wherein the projection structure is a fin structure and the means for laterally retaining comprises at least one lateral projection structure extending outwardly from at least one side of the at least one fin structure, the at least one lateral projection structure adapted to mate with a corresponding channel created in the bone.

18. The implantable orthopedic prosthesis of claim 17, wherein the at least one lateral projection structure includes a pair of lateral projections on opposite sides of the at least one fin structure that together with the at least one fin structure define a generally T-shaped structure.

19. The implantable orthopedic prosthesis of claim 15, wherein the projection structure is comprised of a porous metal capable of lateral fluid communication between generally opposing sides of the projection structure to permit tissue in growth through the projection stature post operatively.

20. The implantable orthopedic prosthesis of claim 15, wherein a depth of the projection structure extends inwardly from the fixation surface of the implant body a distance at least as large as a cross-sectional depth of the implant body at a location other than a location of the projection structure.

21. The implantable orthopedic prosthesis of claim 16, wherein the means for laterally retaining comprises at least one retention aperture defined in the at least one projection structure and a corresponding cross pin adapted to mate with the at least one retention aperture.

22. The implantable orthopedic prosthesis of claim 21, wherein the means for laterally retaining comprises at least two retention apertures defined in the at least one fin structure and a corresponding cross pin adapted to mate with each retention aperture.

23. The implant of claim 16, wherein the means for laterally retaining the at least one projection structure such that a preload force is exerted on the implant body is effected by the advancement of one of a cross pin, a threaded pin, a tapered pin, bone cement, and a flowable material into an aperture formed in bone and into contact with the projection structure after the implant has been brought into contact with the bone.

24. The implantable orthopedic prosthesis of claim 14, wherein the porous bulk construct is a porous metal and the material having a smooth bearing surface is a non-porous metal.

25. The implantable orthopedic prosthesis of claim 14, wherein the implant body has a bulk volume calculable by integrating a surface area of a cross sectional outline of the implant body about a length of the implant body that is normal to the cross sectional outline, and wherein a ratio of an actual displacement volume of the implant body to the bulk volume of the implant body is no more than 1 to 4.

26. The implantable orthopedic prosthesis of claim 14, wherein a depth of the porous bulk construct measured normal to the articulation surface is greater than a depth of the thin layer of the material measured normal to the articulation surface at a location on the implant body that is the same as a location of the depth of the porous bulk construct.

27. The implant of claim 14, wherein the implant body is sufficiently flexible to allow the fixation surface to conform to the resected surface during an expected life cycle of the implantable prosthesis in response to stresses and loads experienced by the implant body.

28. An implantable orthopedic prosthesis for implantation on a resected surface of a bone during an arthroplasty procedure, the implantable prosthesis comprising:

an implant body having a fixation surface facing the bone and an articulation surface adapted to articulate with another implant, the implant body including at least first and second spaced apart fixation features, each fixation feature comprising a projection structure extending inwardly from the fixation surface, the fixation features adapted to be sequentially affixed to the bone, the implant body being a composite of a porous metal forming the fixation surface and a thin layer of a non-porous metal forming the articulation surface, and wherein the fixation surface has a preoperative fixation path adapted to diverge from a cutting path of the resected surface when one of a posterior portion or an anterior portion of the fixation surface is in contact with and fixed to a corresponding posterior portion or anterior portion of the resected surface with the first fixation feature, and the implant is sufficiently flexible to enable a surgeon to force the implant to deform so as to cause the intraoperative fixation path to substantially match the cutting path prior to fixing the other of the posterior portion of the anterior portion of the fixation surface to the bone with the second fixation feature.

* * * * *

UNITED STATES PATENT AND TRADEMARK OFFICE
CERTIFICATE OF CORRECTION

| | |
|---|---|
| PATENT NO. | : 9,814,539 B2 |
| APPLICATION NO. | : 11/075840 |
| DATED | : November 14, 2017 |
| INVENTOR(S) | : Haines |

Page 1 of 1

It is certified that error appears in the above-identified patent and that said Letters Patent is hereby corrected as shown below:

On the Title Page

Page 2, "Related U.S. Application Data" (60) after "60/536,320, filed on" please delete "January 14, 2005" and insert in its place --January 14, 2004--.

Signed and Sealed this
Twentieth Day of March, 2018

Andrei Iancu
*Director of the United States Patent and Trademark Office*